Figure 4:
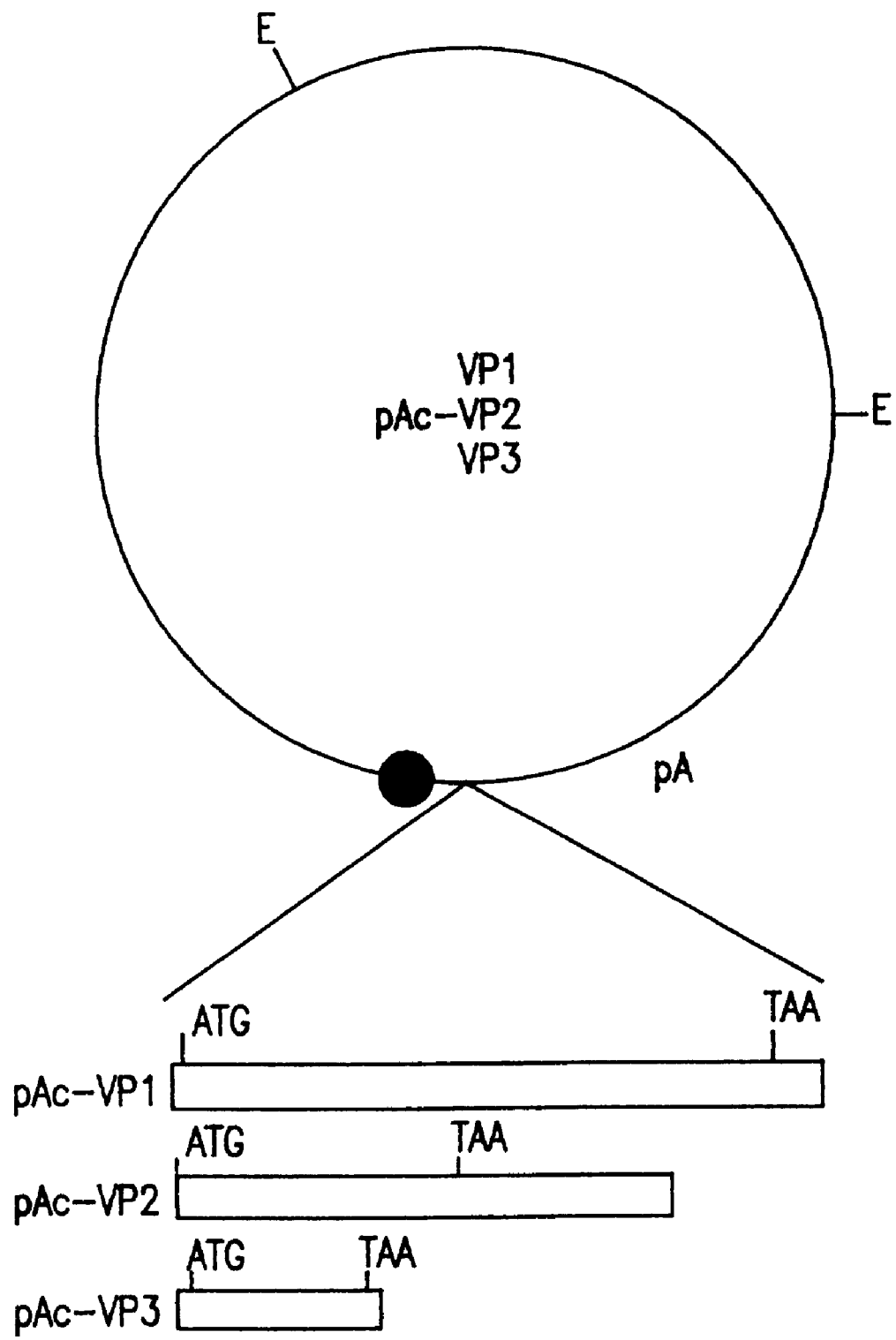

US005922600A

United States Patent [19]
Noteborn et al.

[11] Patent Number: 5,922,600
[45] Date of Patent: Jul. 13, 1999

[54] CHICKEN ANEMIA VIRUS MUTANTS AND VACCINES AND USES BASED ON THE VIRAL PROTEINS VP1 VP2 AND VP3 OR SEQUENCES OF THAT VIRUS CODING THEREFOR

[75] Inventors: Matheus Hubertus Maria Noteborn, Leiden; Guus Koch, Lelystad, both of Netherlands

[73] Assignee: Leadd BV, Netherlands

[21] Appl. No.: 08/489,666

[22] Filed: Jun. 7, 1995

Related U.S. Application Data

[62] Continuation-in-part of application No. 08/454,121, filed as application No. PCT/NL94/00168, Jul. 19, 1994, which is a continuation-in-part of application No. 08/030,335, filed as application No. PCT/NL91/00165, Sep. 11, 1991, Pat. No. 5,491,073.

[30] Foreign Application Priority Data

Sep. 12, 1990 [NL] Netherlands ............................ 9002008
Jul. 20, 1993 [NL] Netherlands ............................ 9301272

[51] Int. Cl.⁶ ............................ C12N 15/86; C12N 15/33; C12N 7/01; C07H 21/04
[52] U.S. Cl. .................. 435/456; 435/235.1; 435/320.1; 435/0.325; 435/0.348; 536/23.1
[58] Field of Search ............................ 435/235.1, 320.1, 435/172.3, 325, 348, 456; 536/23.5, 23.1

[56] References Cited

U.S. PATENT DOCUMENTS 5,554,525  9/1996  Sondermeijer et al. ................ 435/349

FOREIGN PATENT DOCUMENTS 0483911  5/1992  European Pat. Off. ..
0533294  3/1993  European Pat. Off. ..

OTHER PUBLICATIONS

Claessens et. al.. Molecular cloning and sequence analysis of the genome of chicken anaemia agent. J. Gen. Virol. vol. 72:2003–2006, Aug. 1991.

Beard, CW. Avian immunoprophylaxis. Avian Diseases. vol. 23(2):327–334, Dec. 1978.

Rasmussen et al. Characterization of virus–like particles produced by a recombinant baculovirus containing the gag gene of the bovine immunodeficeincy–like virus. Virology. vol. 178:435–451, Jul. 1990.

McNulty et al. Economic effects of subclinical chicken anemia virus agent infection in broiler chickens. Avian Diseases. vol. 35:263–268, Jan. 1991.

Arif. Recent advances in the molecular biology of entomopoxviruses. J. Gen. Virol. 76:1–13, Jan. 1995.

(List continued on next page.)

*Primary Examiner*—James Ketter
*Assistant Examiner*—William Sandals
*Attorney, Agent, or Firm*—Rae-Venter Law Group, P.C.

[57] ABSTRACT

The coding information for three putative chicken anemia virus proteins (VP1, VP2, VP3) was inserted into a baculovirus vector and expressed in insect cells. The immunogenic properties of the chicken anemia virus (CAV) proteins produced separately or together in insect cell cultures were analyzed by inoculating them into chickens. Only lysates of insect cells which have synthesized equivalent amounts of all three recombinant CAV proteins or cells which synthesized mainly VP1 plus VP2 induced neutralizing antibodies directed against CAV in inoculated chickens. Progeny of those chickens were protected against clinical disease after CAV challenge. Inoculation of a mixture of lysates of cells that were separately infected with VP1-, VP2- and VP3-recombinant baculovirus did not induce significant levels of neutralizing antibody directed against CAV and their progeny were not protected against CAV challenge. Our results indicate that expression in the same cell of at least two CAV proteins, VP1 plus VP2, is required to obtain sufficient protection in chickens. Therefore, recombinant CAV proteins produced by baculovirus vectors can be used as a sub-unit vaccine against CAV infections.

5 Claims, 15 Drawing Sheets

OTHER PUBLICATIONS

Orkin et al. Report and recommendation of the panel to assess the NIH investment in research on gene therapy, Dec. 7, 1995.

Meehan et al. Ehcracterization of viral DNAs from cells infected with chicken anemia agent: sequence analysis of the cloned replicative form and transfection capabilities of cloned genome fragments. Arch. Virol. vol. 124:301–319, Jul. 1992.

Gelderbloom et al., (1989) *Archives of Virol.* 109:115–120.

Jeurissen et al., (1992) *J. Virol.* 66:7383–7388.

Noteborn et al., (1991) *J. Virol.* 65:3131–3139.

Noteborn et al., (1992) *Avian Pathology* 21:107–118.

Noteborn et al., (1992) *Gene* 118:267–271.

Noteborn et al., (1993) In: *Vaccines* 93, CSHL Press. Cold Spring Harbor, USA:299–304.

Ramakrishnan et al., (1993) *Nature* 362:217–223.

Todd et al., (1990) *J. General Virology* 71:819–823.

Todd et al., (1991) *Arch. Virol.* 117:129–135.

```
  M   A   R   R   A   R   R   P   R   G   R   F   Y   S   F   ?   R   G   R   W
ATGGCAAGACGAGCTCGCAGACCGAGAGGCCGATTTTACTCCTTCAGAAGAGGACGGTGG    912
  H   H   L   K   R   L   R   R   R   Y   K   F   R   H   R   R   R   Q   R   Y
CACCACCTCAAGCGACTTCGACGAAGATATAAATTTCGACATCGGAGGAGACAGCGGTAT    972
  R   R   R   A   F   R   K   A   F   H   N   P   R   P   G   T   Y   S   V   R
CGTAGACGAGCTTTTAGGAAGGCCTTTCACAACCCCGCCCCGGTACGTATAGTGTGAGG    1032
  L   P   N   P   Q   S   T   M   T   I   R   F   Q   G   V   I   F   L   T   E
CTGCCGAACCCCCAATCTACTATGACTATCCGCTTCCAAGGGGTCATCTTTCTCACGGAA    1092
  G   L   I   L   P   K   N   S   T   A   G   G   Y   A   D   H   M   Y   G   A
GGACTCATTCTGCCTAAAAACAGCACAGCGGGGGGCTATGCAGACCACATGTACGGGGCG    1152
  R   V   A   K   I   S   V   N   L   K   E   F   L   L   A   S   M   N   L   T
AGAGTCGCCAAGATCTCTGTGAACCTGAAAGAGTTCCTGCTAGCCTCAATGAACCTGACA    1212
  Y   V   S   K   I   G   G   P   I   A   G   E   L   I   A   D   G   S   K   S
TACGTGAGCAAAATCGGAGGCCCCATCGCCGGTGAGTTGATTGCGGACGGGTCTAAATCA    1272
  Q   A   A   D   N   W   P   N   C   W   L   P   L   D   N   N   V   P   S   A
CAAGCCGCGGACAATTGGCCTAATTGCTGGCTGCCGCTAGATAATAACGTGCCCTCCGCT    1332
  T   P   S   A   W   W   R   W   A   L   M   M   M   Q   P   T   D   S   C   R
ACACCATCGGCATGGTGGAGATGGGCCTTAATGATGATGCAGCCCACGGACTCTTGCCGG    1392
  F   F   N   H   P   K   Q   M   T   L   Q   D   M   G   R   M   F   G   G   W
TTCTTTAATCACCCAAAGCAGATGACCCTGCAAGACATGGGTCGCATGTTTGGGGGCTGG    1452
  H   L   F   R   H   I   E   T   R   F   Q   L   L   A   T   K   N   E   G   S
CACCTGTTCCGACACATTGAAACCCGCTTTCAGCTCCTTGCCACTAAGAATGAGGGATCC    1512
  F   S   P   V   A   S   L   L   S   Q   G   E   Y   L   T   R   R   D   D   V
TTCAGCCCCGTGGCGAGTCTTCTCTCCCAGGGAGAGTACCTCACGCGTCGGGACGATGTT    1572
  K   Y   S   S   D   H   Q   N   R   W   Q   K   G   G   Q   P   M   T   G   G
AAGTACAGCAGCGATCACCAGAACCGGTGGCAAAAAGGCGGACAACCGATGACGGGGGC    1632
  I   A   Y   A   T   G   K   M   R   P   D   E   Q   Q   Y   P   A   M   P   P
ATTGCTTATGCGACCGGGAAAATGAGACCCGACGAGCAACAGTACCCTGCTATGCCCCCA    1692
  D   P   P   I   I   T   A   T   T   A   Q   G   T   Q   V   R   C   M   N   S
GACCCCCCGATCATCACCGCTACTACAGCGCAAGGCACGCAAGTCCGCTGCATGAATAGC    1752
  T   Q   A   W   W   S   W   D   T   Y   M   S   F   A   T   L   T   A   L   G
ACGCAAGCTTGGTGGTCATGGGACACATATATGAGCTTTGCAACACTCACAGCACTCGGT    1812
  A   Q   W   S   F   P   P   G   Q   R   S   V   S   R   R   S   F   N   H   H
GCACAATGGTCTTTTCCTCCAGGGCAACGTTCAGTTTCTAGACGGTCCTTCAACCACCAC    1872
  K   A   R   G   A   G   D   P   K   G   Q   R   W   H   T   L   V   P   L   G
AAGGCGAGAGGAGCCGGGGACCCCAAGGGCCAGAGATGGCACACGCTGGTGCCGCTCGGC    1932
  T   E   T   I   T   D   S   Y   M   S   A   P   A   S   E   L   D   T   N   F
ACGGAGACCATCACCGACAGCTACATGTCAGCACCCGCATCAGAGCTGGACACTAATTTC    1992
  F   T   L   Y   V   A   Q   G   T   N   K   S   Q   Q   Y   K   F   G   T   A
TTTACGCTTTACGTAGCGCAAGGCACAAATAAGTCGCAACAGTACAAGTTCGGCACAGCT    2052
  T   Y   A   L   K   E   P   V   M   K   S   D   A   W   A   V   V   R   V   Q
ACATACGCGCTAAAGGAGCCGGTAATGAAGAGCGATGCATGGGCAGTGGTACGCGTCCAG    2112
  S   V   W   Q   L   G   N   R   Q   R   P   Y   P   W   D   V   N   W   A   N
TCGGTCTGGCAGCTGGGTAACAGGCAGAGGCCATACCCATGGGACGTCAACTGGGCGAAC    2172
  S   T   M   Y   W   G   T   Q   P   *
AGCACCATGTACTGGGGGACGCAGCCCTGA                                  2201
```

FIG. 1

```
       M   H   G   N   G   G   Q   P   A   A   G   G   S   E   S   A   L   S   R   E
ATGCACGGGAACGGCGGACAACCGGCCGCTGGGGGCAGTGAATCGGCGCTTAGCCGAGAG                          439
     G   Q   P   G   P   S   G   A   A   Q   G   Q   Y   I   S   N   E   R   S   P
GGGCAACCTGGGCCCAGCGGAGCCGCGCAGGGGCAAGTAATTTCAAATGAACGCTCTCCA                          499
     R   R   Y   S   T   R   T   I   N   G   V   Q   A   T   N   K   F   T   A   V
AGAAGATACTCCACCCGGACCATCAACGGTGTTCAGGCCACCAACAAGTTCACGGCCGTT                          559
     G   N   P   S   L   Q   R   D   P   D   W   Y   R   W   N   Y   N   H   S   I
GGAAACCCCTCACTGCAGAGAGATCCGGATTGGTATCGCTGGAATTACAATCACTCTATC                          619
     A   V   W   L   R   E   C   S   R   S   H   A   K   I   C   N   C   G   Q   F
GCTGTGTGGCTGCGCGAATGCTCGCGCTCCCACGCTAAGATCTGCAACTGCGGACAATTC                          679
     R   K   H   W   F   Q   E   C   A   G   L   E   D   R   S   T   Q   A   S   L
AGAAAGCACTGGTTTCAAGAATGTGCCGGACTTGAGGACCGATCAACCCAAGCCTCCCTC                          739
     E   E   A   I   L   R   P   L   R   V   Q   G   K   R   A   K   R   K   L   D
GAAGAAGCGATCCTGCGACCCCTCCGAGTACAGGGTAAGCGAGCTAAAAGAAAGCTTGAT                          799
     Y   H   Y   S   Q   P   T   P   N   R   K   K   A   Y   K   T   V   R   W   Q
TACCACTACTCCCAGCCGACCCCGAACCGCAAAAAGGCGTATAAGACTGTAAGATGGCAA                          859
     D   E   L   A   D   R   E   A   D   F   T   P   S   E   E   D   G   G   T   T
GACGAGCTCGCAGACCGAGAGGCCGATTTTACTCCTTCAGAAGAGGACGGTGGCACCACC                          919
     S   S   D   F   D   E   D   I   N   F   D   I   G   G   D   S   G   I   V   D
TCAAGCGACTTCGACGAAGATATAAATTTCGACATCGGAGGAGACAGCGGTATCGTAGAC                          979
     E   L   L   G   R   P   F   T   T   P   A   P   V   R   I   V   *
GAGCTTTTAGGAAGGCCTTTCACAACCCCCGCCCCGGTACGTATAGTGTGA                                  1030
```

FIG. 2

```
  M   N   A   L   Q   E   D   T   P   P   G   P   S   T   V   F   R   P   P   T
ATGAACGCTCTCCAAGAAGATACTCCACCCGGACCATCAACGGTGTTCAGGCCACCAACA            545
  S   S   R   P   L   E   T   P   H   C   R   E   I   R   I   G   I   A   G   I
AGTTCACGGCCGTTGGAAACCCCTCACTGCAGAGAGATCCGGATTGGTATCGCTGGAATT            605
  T   I   T   L   S   L   C   G   C   A   N   A   R   A   P   T   L   R   S   A
ACAATCACTCTATCGCTGTGTGGCTGCGCGAATGCTCGCGCTCCCACGCTAAGATCTGCA            665
  T   A   D   N   S   E   S   T   G   F   K   N   V   P   D   L   R   T   D   Q
ACTGCGGACAATTCAGAAAGCACTGGTTTCAAGAATGTGCCGGACTTGAGGACCGATCAA            725
  P   K   P   P   S   K   K   R   S   C   D   P   S   E   Y   R   V   S   E   L
CCCAAGCCTCCCTCGAAGAAGCGATCCTGCGACCCCTCCGAGTACAGGGTAAGCGAGCTA            785
  K   E   S   L   I   T   T   T   P   S   R   P   R   T   A   K   R   R   I   R
AAAGAAAGCTTGATTACCACTACTCCCAGCCGACCCCGAACCGCAAAAAGGCGTATAAGA            845
  L   *
CTGTAA                                                                   851
```

FIG. 3

FIG. 8A

Amino-Acid Sequence of VP3.

```
1 -M  N  A  L  Q  E  D  T  P  P  G  P  S  T  V
   F  R  P  P  T  S  S  R  P  L  E  T  P  H  C
   R  E  I  R  I  G  I  A  G  I  T  I  T  L  S
   L  C  G  C  A  N  A  R  A  P  T  L  R  S  A
   T  A  D  N  S  E  S  T  G  F  K  N  V  P  D
   L  R  T  D  Q  P  K  P  P  S  K  K  R  S  C
   D  P  S  E  Y  R  V  S  E  L  K  E  S  L  I
   T  T  T  P  S  R  P  R  T  A  K  R  R  I  R
   L -121
```

FIG. 8B

```
1 - 150
    88   86   83   83   89     86   85   85  105   81     88   91   83   81   81
    83   92   86   83   86    121   86   86  135   83     86   92   86   80   81
    86   88   83   86   97     88   86   86   83   86     92   93   86   83   86
    92   85   86   86   93     85   86   86   86   85     88   81   85   81   83
    88   88   89   83   83     83   88   88  101   86     95   83   86   81   83
    93   92   83   88   85     83   96   88   81   88     93   81   85   81   81
    93   92   85   86   98     83  138   88   83   89     92   83   83   86   83
    93   83   86   85   86     83   85   83   86   85     93   83   81   83   83
    91   88   89   86   86     83   86   83   86   86     93   80   81   83   86
    88   83   86   86   86     86   83   81  122   88     88   83   83   93   86

151 - 300
   114   85   86   85   81     93   83   85  116   81     80   81   81   85   86
    80   86   88   81   86     93   83   86   86   83     81   85   78   83   83
    83   83   86   83   88     91   83   83   81   81     83   83   81   83   83
    83   88   83   85   86     95   88   83   83   85     81   86   83   81   81
    81   83   86   85   88     95   80   81   86   97     85  123   81   83   85
    83   93   83   83   86     91   89   86  106   76     83   86   83   81   86
    83   83   81   83   88     93   85   81   81   73    116   88   85   81   85
    81   86   81   83   93     92  108   86   81   81     85   86   81   83   86
    83   86   83   85   93     93   85   81   80   80     86   85   83   81   89
    83   85   83   86   93     85  103   83   86   81     86   78   86   81   91

301 - 450
    88   83   85   83   91    129   85   81   83   86     86  101   86   81
    89   83   83   78   88    176   85   86   83   85     83   86   83   83
    88   83   81   83   85     86   86   86   80   88     86   88   83   85
    89   85   83   65   83     88   88   81  126   89     81   86   86   81
    88   86   83   76   83     88   93   83   78   88     88   83   86  101
    83   86   83   83   83     86   86   85   83   88    102   83   86   86
   119   86   83   83   83     86   83   86   83   88     89   89   88   86
    81   81  104   78   88     86   83   86   83   86     89   86  136   86
    86   83   86   83   86     83   88   85   85   85     95   88   86
   119   81   83   85  104     86   83   83   85  192     86   85   88
```

```
1 - 150
    78   70  104   80   76    80   81   81   83   81    92   80  116   78   76
    91   73   76   81   78    71   81   91   81   81    78  104   92   85   76
    85   76   78   83   95    78   83   80   83   80    95   75   85   96   78
    76  104   78   83   83    78   83   81   81   81    76   98   93   81   78
    71  106   78   83   78    81   81   86   78   86    73   91   80  102   76
    71   80   83   81   76    78   83   81   80   81    76   76   78   80   83
    73   76   98   81   78    80   83   80   81   91    73   78   80   78   76
    71  133   80   80   73    73   81   83   80   88    93   81   76   78   80
    96   75   71   85   78    78   83   83   78   81    93   83   78   78   78
    73   76   78   80   78    80   83   81   78   81    86   92   81   78   78

151 - 300
    78   75   73   76   76    70
    78   81   78   73   76    76
    76   78   71   78   83    75
    78   78   76   80   71    73
    76   78   75   73   86    80
    80   75   76   76   78    78
    78   73   73   76   76
    78   73   76   76   78
    78   68   76   76  103
    76   73   81   76   71
```

CHICKEN ANEMIA VIRUS MUTANTS AND VACCINES AND USES BASED ON THE VIRAL PROTEINS VP1 VP2 AND VP3 OR SEQUENCES OF THAT VIRUS CODING THEREFOR

CROSS-REFERENCE TO RELATED APPLICATION

This application is continuation-in-part of U.S. Ser. No. 08/454,121, filed Nov. 30, 1995, which is a National Stage filing of PCT/NL94/00168 filed Jul. 19, 1994 which is a continuation in part of U.S. Ser. No. 08/030,335, now U.S. Pat. No. 5,491,073 filed Mar. 8, 1993, which is a National Stage filing of PCT/NL/91/00165 filed Sep. 11, 1991 which disclosure is hereby incorporated by reference.

INTRODUCTION

1. Technical Field

The present invention relates to novel proteins and/or polypeptides of the Chicken Anemia Virus (CAV) together with vaccines and compositions for preventing or treating virus infections in poultry, in particular infections with CAV.

2. Background

Day-old chicks are most susceptible to CAV infections. In these animal lethargy, anorexia and anemia are observed from 10 days after inoculation with CAV. After infection mortality may increase to a maximum of 50%. With increasing age the resistance also increases. Jeurissen et al. (1992) supra have reported that only the hematocrit values of chicks that had been infected with CAV at an age of 1–3 days are decreased. CAV infections of 1–21 days old chicks results in a depletion of in particular the thymus cortex. However, in older chickens CAV can subclinically multiply. CAV infection in order chickens can be determined by the occurrence of serum conversion (McLlroy et al., (1992) Avian Diseases 36:566–574).

The spread of CAV within a flock of chickens substantially occurs via contact infection. Most probable is ingestion of feces or other material contaminated with feces from CAV infected animals. Infection via the air, however cannot be ruled out. Transmission of viruses to offspring via the egg is suggested by Yuasa et al., (1979) Avian Diseases 23:366–385 but by way of experiment vertical transmission of CAV from mother animals to chicks could not be demonstrated by us.

Immune deficiency resulting from the CAV induced deletion of the thymus cortex is considered to be the cause of disease symptoms occurring after secondary infections of normally non-pathogenic agents (De Boer et al., (1992) Tn: Proceedings World's Poultry Congress Symposium, Amsterdam, The Netherlands, 1:262–271); Avian Diseases 33:707–713; Engström, (1988) Avian Pathology 17:23–32; Rosenberger and Cloud, (1989); Von Bülow et al., (1986) J. Vet. Med. B 33:717–726; Yuasa et al., (1980) Avian Diseases 24:202–209). Thus CAV is isolated in animals with Newcastle disease, Marek's disease, infectious bursitis (Gumboro) and in animals with 'blue wing disease' in association with retroviruses. CAV infections lead to increased inoculation reactions, e.g. against Newcastle disease virus.

Maternal antibodies have been found to give an important protection against CAV infection. A recent study under laboratory conditions has shown that maternal immune day-old chicks develop no CAV infection. Day-old chicks can also be protected passively by intravenous injection of antibodies from egg yolks of immune mother animals.

CAV can be multiplied in tissue culture, however, in general the titers so obtained are low. At present MDCC-MSB1 cells (Yuasa, (1983) National Institute of Animal Health Quarterly 23:13–20; Yuasa et al., (1983) ibid, 78–81) are used therefor, in which CAV induces a cytopathogenic effect 48–72 hours after infection. MDCC-MSB1 cells are also used to determine neutralizing antibodies and antibodies directed against CAV by means of immunofluorescence (Von Bülow et al., (1985) J. Vet. Medicine B 32:679–693; Chettle et al., (1991) The Veterinary Record 128:304–306). It has not been found possible so far to attenuate the virulence of CAV by serial passage in MDCC-MSB1 cells.

Older animals do not develop disease symptoms after CAV infection and chicks with maternal antibodies are protected. These data were used in Germany in a vaccination program based on controlled exposure to CAV of 14–16 weeks old mother animals. In the Netherlands this vaccination method is not allowed except at AN experimental level because of the attendant risks. As mentioned above, it is quite possible that CAV can be transmitted to offspring via the fertilized egg. McNulty et al. (1991) Avian Diseases 35:263–268 have recently shown that flocks that are CAV seropositive have production numbers inferior to those of CAV seronegative flocks. Moreover, Immune deficiency in chickens having a subclinical CAV infection has been shown. The possible vertical virus spread and the immune deficiency caused by CAV with (sub) clinical infections renders a control program based on an innocuous vaccine very desirable.

The Chicken Anemia Virus (CAV) is a recently characterized DNA virus (Noteborn and De Boer, (1990) Dutch Patent No. 9002008). It belongs to a new virus family. In young chickens CAV causes anemia by destruction of erythroblastoid precursor cells and immune deficiency by depletion of thymocytes. Lesions occur in the spleen and liver (Jeurissen et al., (1989) Thymus 14:115–123). A recent study has shown that the depletion of thymocytes is caused via apoptosis induced by CAV ((Jeurissen et al., (1992) J. Virology 66:7383–7388).

Gelderblom et al. (1989) Archives of Virology 109:115–120 and Todd et al. (1990) J. Gen. Virology 71:819–823 have shown by means of electron microscopic studies that CAV particles have a T3 icosahedron symmetry and a diameter of 23–25 nm. The CAV particles concentrate after equilibrium sedimentation at a density of 1.33–1.34 g/ml in CsCl.

Todd et al., (1990) supra have shown that isolated virus particles contain only one protein having a molecular weight of 50 kDa. The single-stranded DNA in the CAV particles is in the form of a circular minus strand (Gelderblom et al., (1989, supra; Todd et al, (1990) supra; Noteborn et al., (1991) J. Virology 65:3131–3139). The replicative DNA intermediary was cloned and fully sequenced. The CAV genome is 2319 nucleotides long. On the basis of the genome structure and the DNA sequence the virus cannot be placed into one of the known virus families (Noteborn et al., (1991) supra; Todd et al., (1991) Archives Virology 71:819–823). The CAV genome contains three large, partially or completely overlapping reading frames coding for possible proteins having molecular weights of 51.6, 24.0 and 13.3 kDa. The CAV genome moreover contains one evident promoter/enhancer region and only one polyadenylation signal. Transcription of the replicative DNA intermediary produces a polyadenylated polycistronic RNA molecule of approximately 2100 nucleotides (Noteborn et al., (1992) supra.

SUMMARY

Provided are methods and compositions derived from the Chicken Anemia Virus (CAV) for use in vaccines and other therapeutics, for example. The method of vaccinating host animals against CAV includes induction of neutralized antibodies by way of providing recombinant produced VP1/VP2 compositions.

BRIEF DESCRIPTION OF THE DRAWINGS

Description of the Figures

FIG. 1 (SEQ ID NOS: 3 & 4) gives the DNA sequence and the amino acid sequence of the VP1 protein of Chicken Anemia Virus. The numbering of the CAV DNA sequences is as given in Dutch patent no. 9002008.

FIG. 2 (SEQ ID NOS: 5 & 6) gives the DNA sequence and the amino acid sequence of the VP2 protein of Chicken Anemia Virus. The numbering of the CAV DNA sequences is as given in Dutch patent no. 9002008.

FIG. 3 (SEQ ID NOS: 7 & 8) gives the DNA sequence and the amino acid sequence of the VP3 protein of Chicken Anemia Virus. The numbering of the CAV DNA sequences is as given in Dutch patent no. 9002008.

FIG. 4 shows the diagrammatic representation of the 3 CAV recombinant transfer vectors pAc-VP1, pAc-VP2 and pAc-VP3. ●=polyhedron promoter, ATG=initiation codon, pA=polyadenylation signal, E=EcoRI.

FIG. 5 (SEQ ID NOS: 9–15) shows the pepscan analysis of the monoclonal antibody CVI-CAV-85.1 with peptides (12-mers) derived from VP3. The core sequence PSTVFR (SEQ ID NO: 28), against which the monoclonal CVI-CAV-85.1 is directed, is at positions 12 to 17 of the VP3 amino acid sequence (Noteborn et al., (1991).

FIG. 6 (SEQ ID NOS: 16–20) shows the pepscan analysis of the monoclonal antibody 111.2 with peptides (12-mers) derived from VP2. Monoclonal 111.2 is directed against the epitope GLEDRSTQ (SEQ ID NO: 29) which is at positions 109 to 116 of the VP2 amino acid sequence (NOTEBORN et al., (1991). Only the results obtained with peptides nos. 1 through 140 are shown (extinction of peptides nos. 141 through 206≦0.103).

FIG. 7 (SEQ ID NOS: 21–27) shows the pepscan analysis of the monoclonal antibody 111.3 with peptides (12-mers) derived from VP3. Monoclonal 111.3 is directed against the epitope PTSSR (SEQ ID NO: 30) which is at positions 19 to 23 of the VP3 amino acid sequence (Noteborn et al., (1991).

FIG. 8*a* shows the diagrammatic representation of the 2 expression vectors pRSV-VP3 and pRSV-tr. ■=VP3, ▧=VO3tr, ⊡=RSV LTR, □=SV40. FIG. 8*b*, (SEQ ID NO: 7) shows the amino acid sequence of the CAV protein VP3. The proline residues are printed in italics and the basic amino acids in heavy type. The 11 C terminal amino acids, the codons of which are deleted in the expression vector, are underlined.

FIG. 9 shows the kinetics of the apoptotic effect of VP3 or truncated VP3. MDCC-MSB1 cells were transfected with plasmid pRSV-VP3 (●) or pRSV-tr (○) fixed and stained with the monoclonal antibody CVI-CAV-85.1 at different times after transfection. The percentages of the immunofluorescent cells with nuclei which normally stain with propidium iodide are given. Per experiment at least 100 cells were counted which had expressed VP3 or truncated VP3.

FIG. 10 shows the diagrammatic representation of the expression vectors pCMV-VP3 and pCMV-tr ⊡=CMV promoter, ▨=rabbit B-globin, □=neomycin resistance, ■=VP3 or truncated VP3, ▥=RSV promoter, ▤=pBR322 sequences, B=BamHI cloning site.

FIGS. 11*a* and 11*b* show the kinetics of the apoptotic effect of VP3 on human hematopoietic (tumor) cells. The cell line KG1 was transfected with plasmid pRSV-VP3, and the cell lines DOHH-2, K562 and Jobo-0 were transfected with plasmid pCMV-VP3. The percentages of the VP3-positive cells with nuclei that weakly stain with propidium iodide, apoptotic cells, are given. Per experiment at least 200 cells were counted. For FIG. 11*a*: -○-=KG1, -●-=DOHH-2, -□-=K562, -■-=Jobo-0. For FIG. 11*b*: -○-=K562*pCMV-VP3, -●-=K562*pCMV-trVP3.

FIGS. 12*a* and 12*b* show the kinetics of the apoptotic effect of VP3 on human osteosarcoma cell lines. Cells of the cell lines Saos-2, Saos-2/Ala143 and U2-OS were transfected with plasmid pCMV-VP3. The percentages of the VP3-positive cells with nuclei that weakly stain with propidium iodide, apoptotic cells, are given. Per experiment at least 500 cells were counted. For FIG. 12*a*: -□-=Sa05-2/Alg143, mutant p53, -○-=Sa05-2, p53-, -●-=U2-05, p53t. For FIG. 12*b*: -○-=Sa05-2*pCMV-VP3, -●-=Sa05-2*pCMV-trVP3.

FIG. 13 shows the diagrammatic representation of the recombinant transfer pUW-VP1/VP2.

FIGS. 14*a* and 14*b* show the pepscan analysis of the neutralizing monoclonal antibodies of type 132.1 with peptides (12-mers) derived from VP1. FIG. 14*a* depicts the pepscan data graphically, while FIG. 14*b* depicts the same data numerically.

FIGS. 15*a* and 15*b* show the pepscan analysis of the neutralizing monoclonal antibodies of type 132.1 with peptides (12-mers) derived from VP2. FIG. 15*a* depicts the pepscan data graphically, while FIG. 15*b* depicts the same data numerically.

DESCRIPTION OF SPECIFIC EMBODIMENTS

In particular, the invention related to vaccines that are less pathogenic than the CAV itself but yet lead to the generation of neutralizing antibodies in the immunized animal. Besides, the invention relates to compositions containing antibodies against parts of the CAV for controlling infections with CAV. Also anti-idiotype antibodies which possess an immunogenicity corresponding with the antigen are a subject of the invention. The invention also relates to antibodies for the detection or control of CAV infections. Also diagnostic test kits for the detection of CAV will be described. The invention further relates to recombinant DNA molecules derived from CAV, which code for at least an immunogenic part of a CAV protein and host cells transfected with such recombinant DNA molecules. Vaccines based on these host cells are made possible by this invention. Also so-called living virus vaccines in which a piece of DNA coding for at least an immunogenic part of a CAV protein is brought into a virus infectious to the desired host are a subject of the invention. Processes for the prophylaxis or control of CAV infections, in particular in chickens, and processes for the preparation of recombinant parts of CAV comprising sequences, and processes for the preparation of vaccines are also subjects of the invention. Besides, the invention relates to uses of the proteins of the CAV in the induction of apoptosis (programmed cell death). In particular, the proteins (polypeptides) can be used in the induction of apoptosis in tumor cells. Besides, the proteins according to the invention can also be used in the elimination of other undesired cell populations, such as autoimmune reactive T cells in autoimmune diseases, such a rheumatoid arthritis, lupus, etc. The invention further provides for the induction of cell death by means of gene therapy. Processes for preparing these therapeutics and processes for treatment therewith are also subjects of the invention.

In general, inactivated vaccines and subunit vaccines are the safest vaccines. The fact that under tissue culture conditions CAV multiplies only to low titers renders the preparation of an inactivated vaccine relatively expensive and laborious. For the preparation of a subunit vaccine against CAV infections those CAV proteins are necessary which induce a protective immune response in vaccinated chickens. Thus far only one protein (called VP1) has been found in purified CAV particles.

Surprisingly, it has now been found that this protein alone is not capable of giving an immune response that protects against CAV infections. It has been found that in spite of the fact that VP1 seems to be the only protein present in the virus particle the VP2 protein now expressed by us for the first time is essential for generating virus neutralizing antibodies. Therefore, it is possible only now to develop an effective vaccine on the basis of parts of the virus.

We have cloned the three open reading frames present on the CAV genome into baculovirus vectors. The three CAV proteins VP1, VP2 and VP3 were expressed into Sf9 cells alone, in combination with one of the other CAV proteins or all three simultaneously be means of (co)-infection with recombinant CAV baculoviruses. Mother animals were injected with crude cell lysates which contained one or more CAV proteins. Only after immunization of chickens with antigen preparations containing proportional amounts of all three CAV proteins or containing essentially VP1 and VP2 and also some VP3, neutralizing antibodies developed. Eggs of such animals contained maternal antibodies against CAV. Infection tests with offspring of vaccinated mother animals showed that at least the CAV proteins VP1 and VP2 are necessary for the induction of a protective immune response. Offspring of mother animals injected with all three CAV proteins were even better protected against infections with CAV. Injection into chickens with all three CAV proteins that had each individually been produced in Sf9 cells, induced few neutralizing antibodies against CAV. This implies that for an optimum induction of neutralizing antibodies against CAV two or three CAV proteins must be synthesized together in a host cell.

It is possible that fragments of two or three CAV proteins are already sufficient to effect a protective immune response against CAV infections. The recombinant CAV products, VP1+VP2 or VP1+VP2+VP3, which will be used for vaccination of laying-hens, can be synthesized by means of the baculovirus system. The CAV proteins can also be synthesized by means of other systems, such as bacterial or yeast cells, via retro (viral) infection or gene amplification (CHO-dhfr system). The fact that 2 or 3 proteins encoded by the open reading frames of the CAV genome can induce a protective immune response in chickens is also applicable to the development of living virus vectors. The coding sequences for VP1+VP2 or VP1+VP2+VP3 are then cloned into living virus vectors. It is also possible that one of the CAV proteins VP1, VP2 or VP3, separately, but then within the context of a living virus vector, is also suitable for the induction of a protective immune response against CAV infections. The expression of fragments of one or more above-mentioned CAV proteins by living virus vectors may be sufficient for the induction of a protective immune response.

In poultry, only living virus vectors which themselves show a good replication in the avian system can be used. Eligible for the use of viral vectors in chickens are, among other things: fowl pox virus, retroviral vectors, herpes virus vectors (Marek's virus and turkey herpes virus), adenoviruses and laryngotracheitis virus. It has been found that the induction of cell death as induced by CAV can essentially be attributed to VP3 and partly to VP2.

By deletion of the C terminal 11 amino acids of VP3 the induction of apoptosis by VP3 is strongly reduced. Consequently, the pathogenic activity of CAV can be drastically reduced by introduction of a stop codon into the C terminal region of VP3. The extra stop codon in the coding region for VP3 is introduced into the CAV clone pCAV/EcoRI (Noteborn and De Boer, Dutch Patent No. 9002008) which contains the complete CAV genome. The complete CAV mutant genome is cut from the vector and recycled. MDCC-MSB1 cells are transfected with the recycled CAV mutant DNA, and the virus offspring which are less pathogenic are harvested. Chickens are vaccinated with the attenuated CAV mutant viruses. Since the VP2 protein also has an effect on the induction of apoptosis, it is possible to also prepare attenuated CAV which contains a mutation in the coding region for VP2 or VP2 and VP3. The above-mentioned introduction of a stop codon into the coding region for VP2 and/or VP3 can also be used in the production of CAV recombinant living virus vectors.

Animals infected with CAV at an older age develop no clinical symptoms. Yet it seems that such infections may lead to great economic losses for the poultry industry. Immunization of animals with the above-described recombinant CAV products will lead to an active protection against the above-mentioned subclinical symptoms. The three CAV proteins which were expressed into the baculovirus system separately or in combination with one or two other CAV proteins can be used for tracing antibodies directed against CAV. Chickens infected or vaccinated with CAV can thus be traced. One or more CAV proteins can be used in immuneassays, such as enzyme-linked immunosorbent assay (ELISA), immunoperoxidase staining and immunofluorescence assay. For measuring neutralizing antibodies two or more CAV proteins are required.

Immunization of mice with the three CAV recombinant products synthesized in insect cells with CAV recombinant baculoviruses finally produced monoclonal antibodies specific for VP2 and VP3. These monoclonals reacted with specific structures in CAV infected calls and not with uninfected cells.

By means of the antibodies generated with recombinant CAV proteins, CAV proteins can be traced in organ preparations of CAV-infected chickens. On the basis of these data, reliable diagnostic tests can be developed. The monoclonal and polyclonal antibodies according to the invention also may be used in other diagnostic assays, such as ELISAs, RIAs, SPIAs, immunofluorescence assays and immunoperoxidase staining, optionally together with one or more CAV proteins or fragments thereof.

In principle, all known embodiments of immunological diagnostic tests are possible with all available labels, and depending on the test to be carried out and the conditions under which it must be carried out, a person of ordinary skill in the art will be able to select the most suitable embodiment. Besides, for the purpose of this invention antibodies and/or other proteins/polypeptides are also derivatives and/or fragments, as far as they possess the desired activity for use in an immunological diagnostic test. In the case of antibodies this means that they must at least be able to recognize the antigen.

The antibodies according to the invention also may be used for the passive immunization of poultry. Against the antibodies according to the invention antibodies can be generated which are a so-called "internal image" of the antigen and can thus be used as such again, in particular in passive immunizations and diagnostics.

The invention will be explained in more detail on the basis of the following experimental part. This is only for the purpose of illustration and should not be interpreted as a limitation of the scope of protection.

EXAMPLES

Materials and Methods

Chickens and Housing

Specific-pathogen-free (SPF) white leghorn strain A (WLA) chickens were obtained from the animal production facility of the DLO institute of Animal Science and Health, Lelystad, The Netherlands. The chickens were kept in conventional chicken houses and therefore vaccinated against Newcastle disease and infectious bronchitis at three weeks of age, for infectious bursal disease at four to five weeks of age, and revaccinated for bronchitis at 11 weeks of age and Newcastle disease at 13 weeks of age.

To obtain chicks with maternal antibodies directed against CAV, eggs of chickens immunized with recombinant CAB-proteins were collected and yolk extracts were tested for maternal antibodies in a CAV neutralization test. Shortly thereafter, fertilized eggs of animals that produced eggs with neutralizing antibodies were collected, incubated and transferred to modified Horsfall-Bauer isolators at hatch.

Baculovirus, insect cells and chicken T cells

The recombinant baculovirus pAcRP23-lacZ (Bishop, (1992) In: Baculovirus and recombinant protein production processes (Eds. Valk, et al. Editiones Roche, F. Hoffmann-La Roche Ltd., Basel, Switzerland) was obtained from Dr. R. Possee NERC Institute of Virology, Oxford, England, and the genomic DNA was purified as described by the method of Summers and Smith (1987) Methods for Baculovirus Vectors and Insect Cell Culture Procedures. Texas Agricultural Experiment Station Bulletin No. 1555. *Spodopiera frugiperda* (Sf9) cells were obtained from the American Tissue Culture Collection (no. CRL 1711). Baculovirus stocks were grown in confluent monolayers and suspension cultures in TC-100 medium (Gibco/BRL) containing S-10% fetal calf serum as described by Summers and Smith (1987) supra.

The T cell line MDCC-MSB1 transformed with Marek's disease virus (Yuasa, (1983) National Institute of Animal Health Quarterly 23:13–20: Yuasa et al., (1983) National Institute of Animal Health Quarterly 23:78–81) was grown in RPMI-1680 medium (Gibco/BRL) containing 10% fetal calf serum; the cells were used for DNA transection experiments.

Example 1

Recombinant Synthesis of CAV Protein

Cloning of CAV DNA: Construction of Recombinant CAV Transfer Vectors

All CAV DNA sequence are originally derived from the plasmid DNA pIc-20H/CAV-EcoRI (Noteborn and DeBoer, (1990), Dutch Patent No. 9002008). All cloning steps with plasmid DNA were in principle carried out according to the methods described by Maniatis et al. (1982) Moleculara Clong; A Laboratory Manual. New York: Cold Spring Harbor Laboratory.

The CAV genome contains three large open reading frames which partially or completely overlap each other. By using start codons in different reading frames the CAV genome codes for three unique proteins. The coding sequences for the CAV proteins were separately (VP1, FIG. 1: VP2, FIG. 2; and VP3, FIG. 3) cloned into the baculovirus transfer vector pAcYM1. (Matsuura et al., (1987) J. General Virology 68:1233–1250), which was obtained from Dr. D. H. L. Bishop, NERC Institute of Virology, Oxford, England. Because the VP3 reading frame completely falls within the VP2 reading frame, VP3, in case of expression of VP2, is always synthesized too, though in a clearly lesser degree. The transfer vector pAcYM1 lacks the coding sequences for polyhedron, the polyhedron promoter inclusively contains the A-residue of the start codon for the polyhedron gene and the 3'-non-coding sequences including the polyadenylation signal. On both sides of the polyhedron sequences are flanking viral sequences. The transfer vector contains prokaryote sequences for multiplication in bacteria (Matsuura et al., (1987) supra).

The plasmid pEP-51.6 (Noteborn et al., (1992) Gene[2] 118:267–271) contains CAV DNA sequences of positions 791 to 2319. The CAV DNA insertion contains the complete coding region for the protein VP1 flanked by 62 bp 5'- an 117 bp 3'-non-coding DNA sequences. The plasmid pEP-51.6 was partially cut with HindIII, then completely cut with EcoRI, and the 'sticky ends' were filled by means of Klenow polymerase. A 1.53 kb CAV DNA fragment was isolated. The plasmid pAcYM1 was linearized with BamHI, the sticky ends filled by means of Klenow polymerase and finally treated with calf intestine alkaline phosphatase (CIP). The 1.53 kb CAV DNA fragment was ligated at the linearized pAcYM1 DNA. The orientation of VP1 in pAcYMI DNA was determined by restriction enzyme analysis, and the final construct pAcVP1 is shown in FIG. 4.

To generate a recombinant transfer vector containing VP2-coating sequences, plasmid pEP-24.0, which contains the 1.15 kb BamHI DNA fragment with CAV DNA sequences of positions 354 to 1508 (Noteborn and De Boer, (1990) supra) was used. This CAV DNA fragment contains the coding region for VP2 flanked by 26 bp 5'- and 484 bp 3'-non-coding DNA sequences. 106 bp downstream of the start codon for VP2 the start codon for VP3 is found in another reading frame, and the other coding sequence for VP3. The plasmid pEP-24.0 was treated with BamHI; the 1.15 kb DNA fragment was isolated and ligated into at the BamHI linearized and CIP treated 9.3 kb pAcYM1 plasmid. The final DNA construct pAcVP2 was characterized with restriction enzymes and is shown in FIG. 4.

To construct a transfer vector with sequences coding VP3, plasmid pEP-13.3 was used which contains the 0.46 kb BamHI-EcoRI DNA fragment with CAV DNA sequences of positions 427 to 868 (Noteborn and De Boer, (1990)). The CAV DNA fragment contains the coding region for VP3, 58 bp 5'- and 25 bp 3'-non-coding DNA sequences. Plasmid pEP-13.3 was cut with the restriction enzymes BamHI and EcoRI, and a 0.46 kb BamHI-EcoRI fragment was isolated. Transfer vector pAcYM1 DNA was linearized with BamHI and treated with CIP, and a 9.3 kb fragment was isolated. The two synthetic DNA oligomers 5'-GATCCAACCCGGGTTG-3' (SEQ ID NO: 1) and 5'-AATTCAACCCGGGTTG-3' (SEQ ID NO: 2) were hybridized to each other and together form a BamHI-EcoRI DNA liner. The DNA linker was ligated at the 0.46 BamHI-EcoRI, and the 9.3 kb BamHI DNA fragment. The final construct pAc-VP3 was analyzed by restriction enzyme digestions and is shown in FIG. 4.

DNA transformations were carried out in the *E. coli* strain HB101. All plasmids were multiplied in large cultures under agitation, purified on CsCl gradients, and then by filtration over SEPHACRYL S-500 columns.

DNA Transfection: Construction of Recombinant CAV Baculovirus

DNA of the recombinant baculovirus AcRP23-lacZ was isolated from extracellular baculoviruses according to a method described by Summers and Smith (1987) supra. The lacZ gene contains a unique cutting site for the restriction enzyme Bsu36I. The AcRP23-lacZ was linearized by digestion with Bsu36I. Sf9 cells were transfected with calcium phosphate precipitates of linearized baculovirus ACRP23-lacZ DNA and recombinant transfer vector DNA according to the method of Smith et al. (1983) Mol. Cell Biol. 3:2156–2165; this is an adaptation of the transection protocol of Graham and Van der Eb (1973) Virology 52:456–467 for Sf9 cells. Each of the three recombinant CAV transfer vectors was transfected separately, together with the recombinant baculovirus AcRP23-lacZ DNA, in Sf9 cells. Transfection occurred with "naked" baculovirus DNA and transfer vector DNA.

For the transection of the diverse human and chicken cell lines 10 micrograms of pRSV-VP3, pCMV-VP3 pRSV-tr or pRSV-tr DNA were resuspended in 25 microliters of Milli-Q water and mixed with 260 microliters of TBS buffer. 15 microliters of 10 mg/ml DEAE dextran were added to the DNA mixture which was incubated for 30 minutes at room temperature. The cells were centrifuged at 1500 rpm in a table centrifuge. The medium was replaced by 5 ml TBS buffer, and the cells were carefully resuspended. The cells were pelleted, and the TBS buffer was removed. The cell pellet was carefully resuspended in 300 microliters of DEAE dextran/DNA mix and incubated for 30 minutes at room temperature. 0.5 ml 25% DMSO/TBS were added, and the suspension was incubated for 3 minutes at room temperature. 5 ml TBS were added, and the cells were centrifuged at 1500 rpm in a table centrifuge. The supernatant was removed, and 5 ml tissue medium were added. The cells were resuspended, centrifuged, taken up in 5 ml tissue culture medium and incubated at 37° C.-5% $CO_2$.

Selection of Recombinant CAV Baculovirus

The AcRP23-lacZ baculovirus genome contains, instead of the polyhedron gene, the lacZ gene, under the regulation of the polyhedron promoter. After homologous recombination baculoviruses were obtained which had always incorporated one of the three CAV genes instead of the lacZ gene and thus under regulation of the promoter of the polyhedron gene. The baculoviruses which have correctly incorporated the CAV gene no longer contain the lacZ gene. In the first instance, the recombinant CAV viruses were characterized for the absence of β-galactosidase activity in plaques of baculovirus infected insect cells. The supernatants containing extracellular baculoviruses were analyzed in a plaque essay with neutral red (Brown and Faulkner, (1977) J. Gen. Virol. 36:361–364) and X-gal (Brown et al., (1991) J. Virol. 65:2702–2706). The lacZ-negative plaques were inoculated on a monolayer of Sf9 cells in microtiter dishes. Five days after infection the supernatants were harvested and stored at 4° C.

Further the integration of CAV DNA sequences in the baculovirus genome was determined by means of a CAV-specific DNA probe in a hybridization experiment. The cell lysates were analyzed in a dot slot hybridization assay with 32P labeled pIc-20H/CAV-EcoRI DNA as a probe.

Expression of the CAV Proteins in Sf9 Cells

The expression of the specific CAV proteins in Sf9 cells infected with recombinant CAV was analyzed by protein labeling with 3H leucine and PAA-SDS gel electrophoresis. Monolayers of Sf9 cells were inoculated with supernatants of cell lysates which strongly hybridized with the labeled CAV DNA probe. Two days after infection the cells were labeled with $^3H$ leucine. The proteins were separated on 14% polyacrylamide (PAA) SDS gels (Laemmli, (1970) Nature 227:680–685, made visible by means of a fluorography method and tested for the presence of specific recombinant CAV protein and the absence of the β-galactosidase protein.

Synthesis of Crude CAV Protein Preparations

Recombinant CAV baculoviruses which expressed the expected CAV protein in infected Sf9 cells, were dished up according to the method described by Summers and Smith (1983) supra. Monolayers of Sf9 cells were infected with one type of recombinant CAV baculovirus having a multiplicity of infection (moi) of approximately 5 plaque-forming units (pfu) per cell. Co-infections of two or three different CAV recombinant baculoviruses were carried out on Sf9 cell monolayers having a mio of 10 pfu of each recombinant CAV baculovirus per cell. Three days after infection the infected Sf9 cells were harvested. The crude cell lysates were suspended in PBS buffer.

The CAV protein VP1 has a calculated molecular weight of 51.6 kDa (Noteborn and De Boer, (1990) supra). Lysates of insect cells infected with recombinant VP1 baculovirus contain a protein of 52 kDa beside baculoviral and cellular products. The 52 kDa protein was absent in lysates of insect cells infected with the baculovirus AcRP23-lacZ and in non-infected cells. In vitro expression of the coding sequence of VP1 resulted in a protein of 52 kDa (Noteborn and De Boer, (1992) supra). Most probably, VP1 is not glycosylated because VP1 which is synthesized in a rabbit reticulocyte lysate and VP1 synthesized in insect cells have the same molecular weight.

Translation of the gene coding for VP2, but also containing all coding sequences for VP3, produced in an in vitro system specific CAV proteins of 30 and 28 kDa and a minor amount of a 16 kDa protein product. Translation of only the open reading frame coding for VP3 in an in vitro system, however, produced only a protein of 16 kDa. Expression of VP2 by recombinant VP2 baculovirus in infected insect cells produced specific products of approximately 28 kDa and 30 kDa. Sf9 cells infected with a recombinant-lacZ baculovirus do not contain these CAV-specific proteins. The Cav-specific product of 16 kDa could mostly be demonstrated in very small amounts only. These data show that the recombinant VP2 baculovirus strongly expresses the protein VP2 and expresses VP3 in but a minor degree. A possible explanation thereof is that an internal start codon in a gene lying on the baculovirus genome is used very inefficiently.

Recombinant VP3 baculovirus synthesized in infected insect cells a main product of 16 kDa and small amounts of some proteins having molecular weights of approximately 21,000 and 12,000–14,000. In an immunofluorescence assay the CAV-specific monoclonal antibody CVI-CAV-85.1 reacted specifically with Sf9 cells expressing VP3. This monoclonal antibody precipitated specifically only a protein having a molecular weight of 16,000 from lysates of radioactively labeled Sf9 cells infected with VP3 recombinant baculovirus. In a pepscan analysis (Geysen et al., 1984) the epitope of the monoclonal antibody CVI-CAV-85.1 was localized on the N-terminus of VP3. The pepscan analysis is shown in FIG. 5.

Example 2

Immunization of Chickens with CAV-Specific Proteins

Induction of Neutralizing Antibodies in Chickens Immunized with Recombinant CAV Proteins In case of chicken anemia it has been determined that neutralizing antibodies properly correlate with protection. The CAV protein or several CAV proteins inducing neutralizing antibodies in chickens thus form the basis of a subunit vaccine.

In the first instance we have examined which CAV protein is capable of inducing antibodies against CAV neutralizing in chickens. Groups of 8 chickens at an age of approximately 6 weeks were injected with lysates of $10^6$ or $10^5$ recombinant CAV-infected Sf9 cells emulsified in complete Freund's adjuvant. As a control a group of 8 chickens was injected with PBS buffer emulsified in complete Freund's adjuvant. Before the immunization and 2, 4 and 6 weeks after immunization blood samples were taken. None of the control animals injected with PBS in complete Freund's adjuvant developed neutralizing antibodies against CAV (Table 1). Also chickens injected with lysates of $10^6$ or $10^8$ insect cells infected with recombinant VP2 or recombinant VP3 baculoviruses developed no neutralizing antibodies against CAV. Of the chickens injected with lysate of $10^5$ infected recombinant VP1 baculovirus insect cells three chickens, and of the chickens infected with a dosage of $10^8$ infected cells two chickens developed low titers varying between 1:8 and 1:32. We conclude that the three recombinant CAV proteins, if infected separately into the chicken, induce no or only very slightly neutralizing antibodies against CAV.

Subsequently, we have studied whether the combination of the three recombinant CAV proteins is capable of inducing neutralizing antibodies in the chicken. To this end, Sf9 cells were infected simultaneously with the three recombinant CAV baculoviruses. Crude lysates of $10^6$ or $10^5$ of the infected cells, which therefore contained recombinant VP1+VP2+VP3, were prepared. Groups of eight chickens at an age of 6–8 weeks were injected with these lysates emulsified in complete Freund's adjuvant. As a control a group of eight chickens was injected.

TABLE 1

Induction Of Neutralizing Antibodies After Immunization With Recomibinant Vp1

| Chicken No. | Antigen Dose# | Neutralization Titer on Day 0 | 14 | 28 | 42 |
|---|---|---|---|---|---|
| 1 | 0{ | ≦4 | ≦4 | ≦4 | ≦4 |
| 2 | 0 | ≦4 | ≦4 | ≦4 | ≦4 |
| 3 | 0 | ≦4 | ≦4 | ≦4 | ≦4 |
| 4 | 0 | ≦4 | ≦4 | ≦4 | ≦4 |
| 5 | 0 | ≦4 | ≦4 | ≦4 | ≦4 |
| 6 | 0 | ≦4 | ≦4 | ≦4 | ≦4 |
| 7 | 0 | ≦4 | ≦4 | ≦4 | ≦4 |
| 8 | 0 | ≦4 | ≦4 | ≦4 | ≦4 |
| 9 | $10^6$ | ≦4 | ≦4 | ≦4 | ≦4 |
| 10 | $10^6$ | ≦4 | 8 | 32 | 8 |
| 11 | $10^6$ | ≦4 | ≦4 | ≦4 | ≦4 |
| 12 | $10^6$ | ≦4 | ≦4 | 8 | ≦4 |
| 13 | $10^6$ | ≦4 | ≦4 | ≦4 | ≦4 |
| 14 | $10^6$ | ≦4 | ≦4 | ≦4 | 16 |
| 15 | $10^6$ | ≦4 | ≦4 | ≦4 | ≦4 |
| 16 | $10^6$ | ≦4 | ≦4 | ≦4 | ≦4 |
| 17 | $10^8$ | ≦4 | ≦4 | ≦4 | ≦4 |
| 18 | $10^8$ | ≦4 | ≦4 | ≦4 | ≦4 |
| 19 | $10^8$ | ≦4 | ≦4 | 8 | 8 |
| 20 | $10^8$ | ≦4 | ≦4 | ≦4 | ≦4 |
| 21 | $10^8$ | ≦4 | ≦4 | ≦4 | ≦4 |
| 22 | $10^8$ | ≦4 | ≦4 | ≦4 | 8 |
| 23 | $10^8$ | ≦4 | ≦4 | ≦4 | ≦4 |
| 24 | $10^8$ | ≦4 | ≦4 | ≦4 | ≦4 | member of SF9 insect cells infected with recombinant baculovirus. Immunization was carried out with cell lysate.
{animals injected with PBS instead of cell lysate with PBS buffer emulsified in complete Freund's adjuvant. Five weeks after immunization the eight chickens immunized with lysate of $10^6$ infected cells were all found to have neutralizing titers between 32 and 256, whereas seven of the eight animals immunized with $10^6$ cells had titers between 16 and 512 (Table 2A). Seven weeks after immunization all the animals of both groups were found to have developed a neutralizing titer against CAV. The group of chickens injected with PBS buffer was found to have developed no demonstrable neutralizing immune response against CAV.

Is it really necessary for the induction of neutralizing antibodies against CAV that the three CAV proteins are synthesized simultaneously in insect cells? To answer this question, Sf9 cells were infected separately with VP1, VP2 and VP3 recombinant baculoviruses. Then the crude cell lysates were combined, mixed with FReund's adjuvant and injected into a group of 8 chickens. As control preparations a crude lysate of Sf9 cells which all synthesized the 3 CAV proteins a simultaneously and PBS buffer were used. Both preparations were emulsified in complete Freund's adjuvant and then injected into separate groups of each 8 chickens.

Sera of the group of chickens injected with crude lysates of Sf9 cells in which the 3 CAV proteins were synthesized separately found to contain no or only very few neutralizing antibodies against CAV. However, the animals of the control group injected with crude lysates of Sf9 cells which together synthesized the 3 CAV proteins were found, as expected, to have developed a neutralizing immune response. The animals infected with CBS buffer were found to be negative (Table 2B).

Neutralizing Antibodies in Eggs of Immunized Mother Animals

The above immunization experiments shown that 3 recombinant CAV proteins expressed together in Sf9 cells induced neutralizing antibodies against CAV. In a next experiment it was examined whether combinations of 2 CAV proteins were also capable of inducing neutralizing antibodies. Here the antibodies in the yolks of eggs of immunized mother animals were measured.

TABLE 2A

Induction Of Neutralizing Antibodies With Immunization With Recomibinant Vp1, VP2 plus VP3

| Chicken No. | Antigen Dose# | Neutralization Titer on Day 15 | 35 | 42 |
|---|---|---|---|---|
| 1 | 0{ | ≦4 | ≦4 | ≦4 |
| 2 | 0 | ≦4 | ≦4 | ≦4 |
| 3 | 0 | ≦4 | ≦4 | ≦4 |
| 4 | 0 | ≦4 | ≦4 | ≦4 |
| 5 | 0 | ≦4 | ≦4 | ≦4 |
| 6 | 0 | ≦4 | ≦4 | ≦4 |
| 7 | 0 | ≦4 | ≦4 | ≦4 |
| 8 | 0 | ≦4 | ≦4 | ≦4 |
| 9 | $10^6$ | 32 | 256 | 1024 |
| 10 | $10^6$ | 8 | 32 | 64 |
| 11 | $10^6$ | ≦4 | 64 | 256 |
| 12 | $10^6$ | 8 | 32 | 128 |
| 13 | $10^6$ | 4 | 64 | 128 |
| 14 | $10^6$ | ≦4 | 16 | 256 |
| 15 | $10^6$ | 8 | ≧128 | 256 |
| 16 | $10^6$ | 4 | ≧128 | 1024 |
| 17 | $10^8$ | 32 | ≦4 | 4 |
| 18 | $10^8$ | 8 | 512 | 256 |
| 19 | $10^8$ | 16 | 64 | 64 |
| 20 | $10^8$ | ≦4 | 64 | 256 |
| 21 | $10^8$ | ≦4 | 16 | 32 |
| 22 | $10^8$ | ≦4 | 32 | 128 |
| 23 | $10^8$ | 16 | 64 | 256 |
| 24 | $10^8$ | 4 | 64 | 128 | member of SF9 insect cells infected with recombinant baculovirus. Immunization was carried out with cell lysate.
{animals injected with PBS instead of cell lysate

TABLE 2B

Induction Of Neutralizing Antibodies After Immunization of Crude Lysates of Sf9 Cells Co-Infected with VP1, VP2, and VP3 Recombinant Baculovirus, of Mixture of Crude Lysated of Sf9 Cells Separately Infected with VP1, VP2, and VP3 Recombinant Baculovirus

| Chicken No. | Immunization | Neutralization Titer on Day | | | |
|---|---|---|---|---|---|
| | | 0 | 14 | 28 | 42 |
| 1042 | PBS | ≤2 | ≤2 | ≤2 | ≤2 |
| 1044 | PBS | ≤2 | ≤2 | ≤2 | ≤2 |
| 1046 | PBS | ≤2 | ≤2 | ≤2 | ≤2 |
| 1048 | PBS | ≤2 | ≤2 | ≤2 | ≤2 |
| 1051 | PBS | ≤2 | ≤2 | ≤2 | ≤2 |
| 1053 | PBS | ≤2 | ≤2 | ≤2 | ≤2 |
| 1056 | PBS | ≤2 | ≤2 | ≤2 | ≤4 |
| 1084 | PBS | ≤2 | ≤2 | ≤2 | ≤2 |
| 1058 | together | ≤2 | ≤2 | 128 | 256 |
| 1060 | together | ≤2 | 16 | 512 | 512 |
| 1062 | together | ≤2 | ≤2 | 64 | 128 |
| 1064 | together | ≤2 | 16 | 128 | 256 |
| 1066 | together | ≤2 | 4 | 64 | 64 |
| 1068 | together | ≤2 | 16 | 256 | N.D. |
| 1070 | together | ≤2 | 16 | 128 | 512 |
| 1072 | together | ≤2 | 16 | 256 | 512 |
| 1074 | apart[&] | ≤2 | ≤2 | 8 | 8 |
| 1078 | apart | ≤2 | 2 | ≤2 | ≤2 |
| 1081 | apart | ≤2 | 2 | ≤2 | ≤2 |
| 1083 | apart | ≤2 | ≤2 | ≤2 | ≤2 |
| 1085 | apart | ≤2 | ≤2 | 2 | 8 |
| 1087 | apart | ≤2 | ≤2 | ≤2 | ≤2 |
| 1089 | apart | ≤2 | ≤2 | ≤2 | ≤2 |
| 1091 | apart | ≤2 | ≤2 | ≤2 | ≤2 | immunization with crude lysates of Sf9 cells co-infected with VP1, VP2, and VP3-recombinant baculovirus.
[&]Immunization with mixtures of crude lysates of Sf9 cells separately infected with VP1, VP2, and VP3 recombinant baculovirus.

Four groups of each 16 hens at an age of 33 weeks were injected with crude lysates of 2×107 Sf9 cells, which were simultaneously infected with VP1, VP2, and VP3 recombinant baculoviruses; or with VP1 and VP2; or with VP1 and VP3; or with VP2 and VP3 recombinant baculoviruses. The cell lysates were emulsified in an equal volume of complete Freund's adjuvant. As a control a group of 16 hens was injected with PBS buffer in complete Freund's adjuvant. Yolk material of eggs of hens injected with these lysates or with PBS buffer was extracted with chloroform and analyzed for the presence of neutralizing antibodies.

The preparations containing either VPI+VP2+VP3 or VPI+VP2 induced in most animals neutralizing antibodies clearly demonstrable in their eggs (Table 3). The eggs of chickens injected with preparations containing either VPI+VP3 or VP2+VP3 were found to have no clear neutralizing antibody titer in the yolks. Only the yolks of eggs of one of the examined chickens were found to contain low titers of neutralizing antibodies. The eggs of the control group of 16 chickens injected with PBS buffer were found to contain no neutralizing antibodies.

The data from the above-mentioned experiments with recombinant CAV proteins show that VPI+VP2 together are necessary and sufficient for the induction of neutralizing antibodies against CAV infections. However, a minor amount VP3 in the VP1+VP2 preparations cannot be ruled out.

Example 3

Production and Characterization of monoclonal Antibodies Specifically Directed Against CAV Proteins For the production of monoclonal antibodies against CAV mice were injected with crude lysates of Sf9 cells co-infected with VP1, VP2 VP3 recombinant baculoviruses. In total, 9 different hybridoma cell lines producing monoclonal antibodies against CAV antigens were obtained.

The monoclonal antibody CVI-CAV-85.1 was obtained by injecting mice intraperitoneally with CAV injected MDCC-MSB1 cells with incomplete Freund's adjuvant. Finally, spleen cells of the immunized mice were fused with P3X63-Ag8.653 myeloma cells (Noteborn et al., (1991) J. Virology 65:3131–3139).

The other monoclonal antibodies directed against CAV antigens were obtained by injecting crude extracts of Sf9 cells infected with the three CAV recombinant baculoviruses into the spleen of 4 BALB/c mice. The sera of the immunized mice were tested for 7 weeks after immunization for neutralizing antibodies against CAV. The spleen cells of the immunized mice were fused with P3X63-Ag8.653 myeloma cells. Antibodies directed against CAV antigens were tested by different ways: aserum neutralization test; ELISAs based on purified CAV and on crude lysates of Sf9 cells infected with CAV recombinant bacu-

TABLE 3

Neutralizing Antibodies in Egg Yolks of Chicks After Immunization With a Combination of Recombinant VP1, VP2, and VP3

| Animal No. | Immunization | No. of Eggs | Average Titer |
|---|---|---|---|
| 1194 | PBS | 1 | ≦4 |
| 1211 | PBS | 3 | ≦4 |
| 1231 | PBS | 3 | ≦4 |
| 1132 | PBS | 4 | ≦4 |
| 1233 | PBS | 4 | ≦4 |
| 1251 | PBS | 4 | ≦4 |
| 1254 | PBS | 2 | ≦4 |
| 1195 | VP1 + VP2 + VP3 | 5 | ≦4 |
| 1196 | VP1 + VP2 + VP3 | 3 | 16 |
| 1197 | VP1 + VP2 + VP3 | 1 | 4 |
| 1199 | VP1 + VP2 + VP3 | 2 | 64 |
| 1203 | VP1 + VP2 + VP3 | 4 | 22.6 |
| 1205 | VP1 + VP2 + VP3 | 1 | 32 |
| 1206 | VP1 + VP2 + VP3 | 3 | 128 |
| 1207 | VP1 + VP2 + VP3 | 3 | 32 |
| 1208 | VP1 + VP2 + VP3 | 3 | 12.6 |
| 1210 | VPl + VP2 + VP3 | 4 | 32 |
| 1216 | VP1 + VP2 | 3 | 64 |
| 1217 | VP1 + VP2 | 4 | 16 |
| 1218 | VP1 + VP2 | 3 | 64 |
| 1219 | VP1 + VP2 | 4 | 45.2 |
| 1220 | VP1 + VP2 | 3 | 32 |
| 1223 | VP1 + VP2 | 3 | 50.8 |
| 1224 | VP1 + VP2 | 4 | 76 |
| 1226 | VP1 + VP2 | 3 | 40.4 |
| 1227 | VP1 + VP2 | 4 | 19 |
| 1228 | VP1 + VP2 | 2 | 8 |
| 1229 | VP1 + VP2 | 3 | 4 |
| 1230 | VP1 + VP2 | 3 | 32 |
| 1235 | VP1 + VP3 | 3 | ≦4 |
| 1238 | VP1 + VP3 | 3 | ≦4 |
| 1239 | VP1 + VP3 | 1 | ≦4 |
| 1245 | VP1 + VP3 | 3 | ≦4 |
| 1248 | VP1 + VP3 | 2 | ≦4 |
| 1249 | VP1 + VP3 | 3 | ≦4 |
| 1255 | VP2 + VP3 | 3 | ≦4 |
| 1258 | VP2 + VP3 | 5 | ≦4 |
| 1259 | VP2 + VP3 | 4 | ≦4 |
| 1260 | VP2 + VP3 | 4 | ≦4 |
| 1261 | VP2 + VP3 | 4 | ≦4 |
| 1263 | VP2 + VP3 | 3 | ≦4 |
| 1264 | VP2 + VP3 | 4 | 9.6 |
| 1265 | VP2 + VP3 | 3 | ≦4 |
| 1266 | VP2 + VP3 | 3 | ≦4 |
| 1267 | VP2 + VP3 | 2 | ≦4 |
| 1268 | VP2 + VP3 | 3 | ≦4 |
| 1269 | VP2 + VP3 | 3 | ≦4 |
| 1270 | VP2 + VP3 | 4 | ≦4 | lovirus; immunofluorescence tests on CAV infected MDCC-MSB1 or on Sf9 cells infected with CAV recombinant baculovirus; Western blots of crude lysates of Sf9 cells infected with CAV recombinant baculovirus, and immunoperoxidase staining on thymus coupes of CAV infected chickens.

Western blots with CAV antigens produced with the baculovirus expression system showed that the monoclonal antibodies 111.1, 111.2, 111.4, 112.1, 112.2, 120.1 and 120.2 are strongly directed against VP2 and the monoclonal antibodies 111.3 and 120.3 strongly against VP3. The monoclonal antibodies which strongly react with VP2 all show a weak cross reaction with VP3. Conversely, the monoclonal antibodies directed against VP3 show a weak cross reaction with VP2.

Example 4

Analysis of Antibodies Against CAV Antigens
In vitro neutralization test

The sera of chickens and mice infected with crude Sf9 cell lysates or PBS butter were diluted 1:2 or 1:4 and then a two-fold dilution series was made. The diluted sera were incubated for 1 hour with $10^4$-$10_5$ $TCID_{50}$ CAV-Cux-1 (Von Bülow et al., (1983) J. Vet Med. B 30:742–750; Von Bülow, (1985) J. Vet. Medicine B 32:679–693. Approximately one hundred thousand cells of the T cell line MDCC-MSB1 transformed by Marek's disease virus were infected with this mixture of diluted sera and virus. As controls MDCC-MSB1 cells were infected with CAV which was neutralized with a positive CAV antiserum and a negative serum originating from specific pathogen free chickens.

The serum neutralization test showed that none of the monoclonal antibodies obtained had a neutralizing activity against CAV, in spite of the fact that the sera of the immunized mice used for preparing the hybridomas did have a neutralizing activity against CAV.

Figure 5:
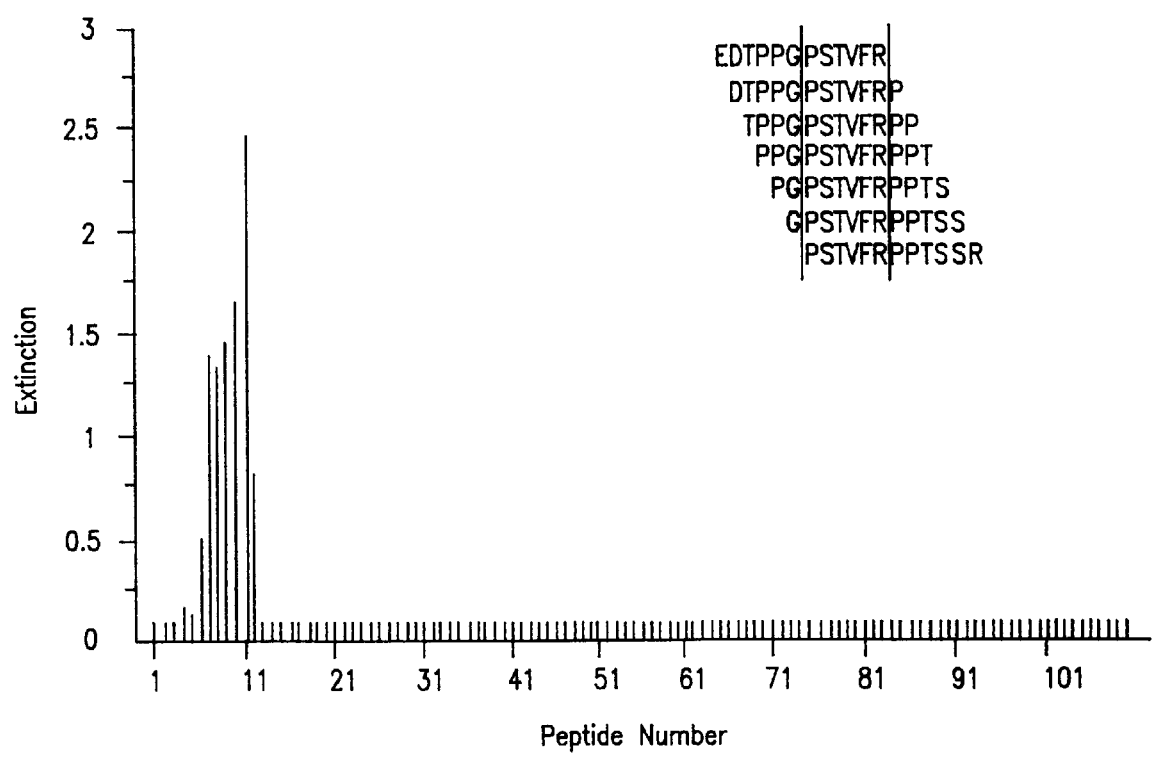
Figure 6:
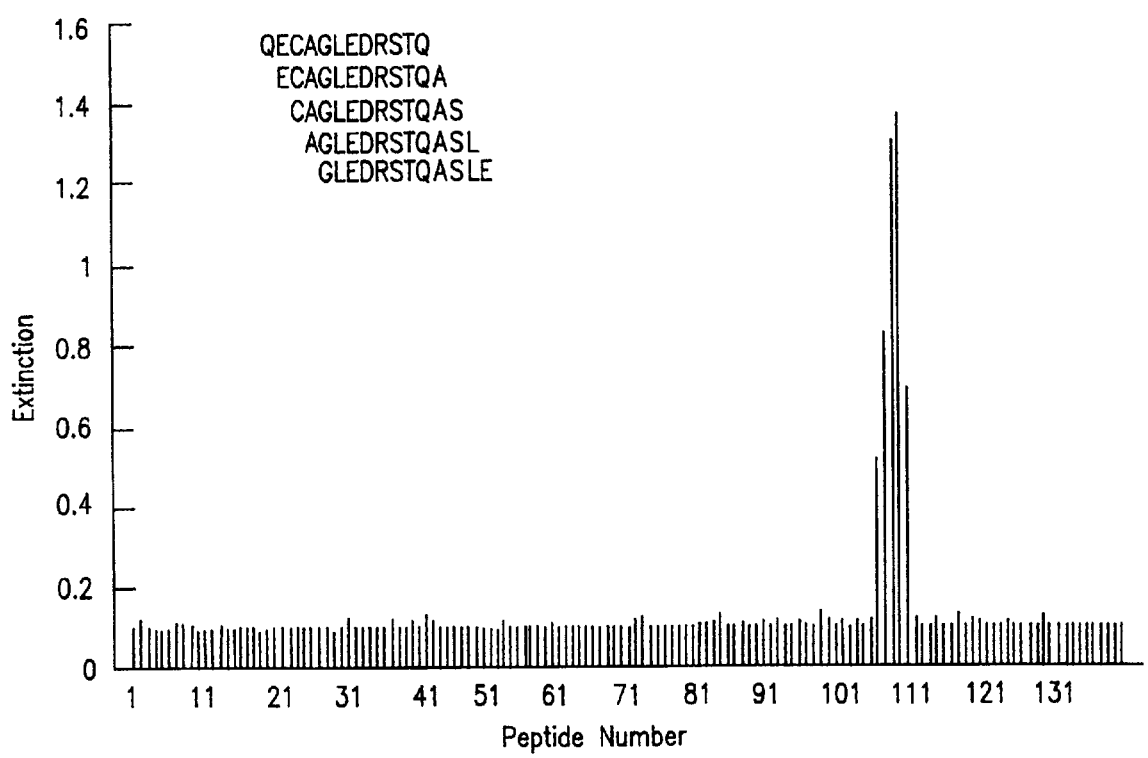
Figure 7:
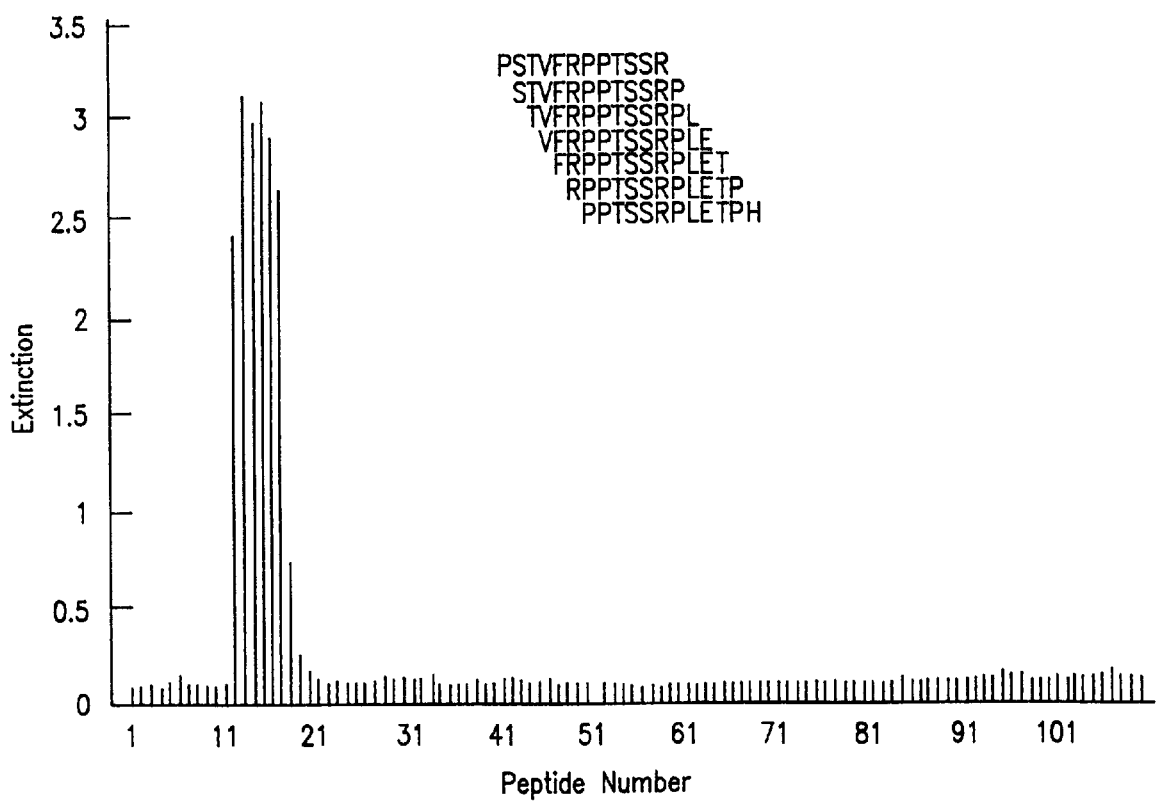
Figure 9:
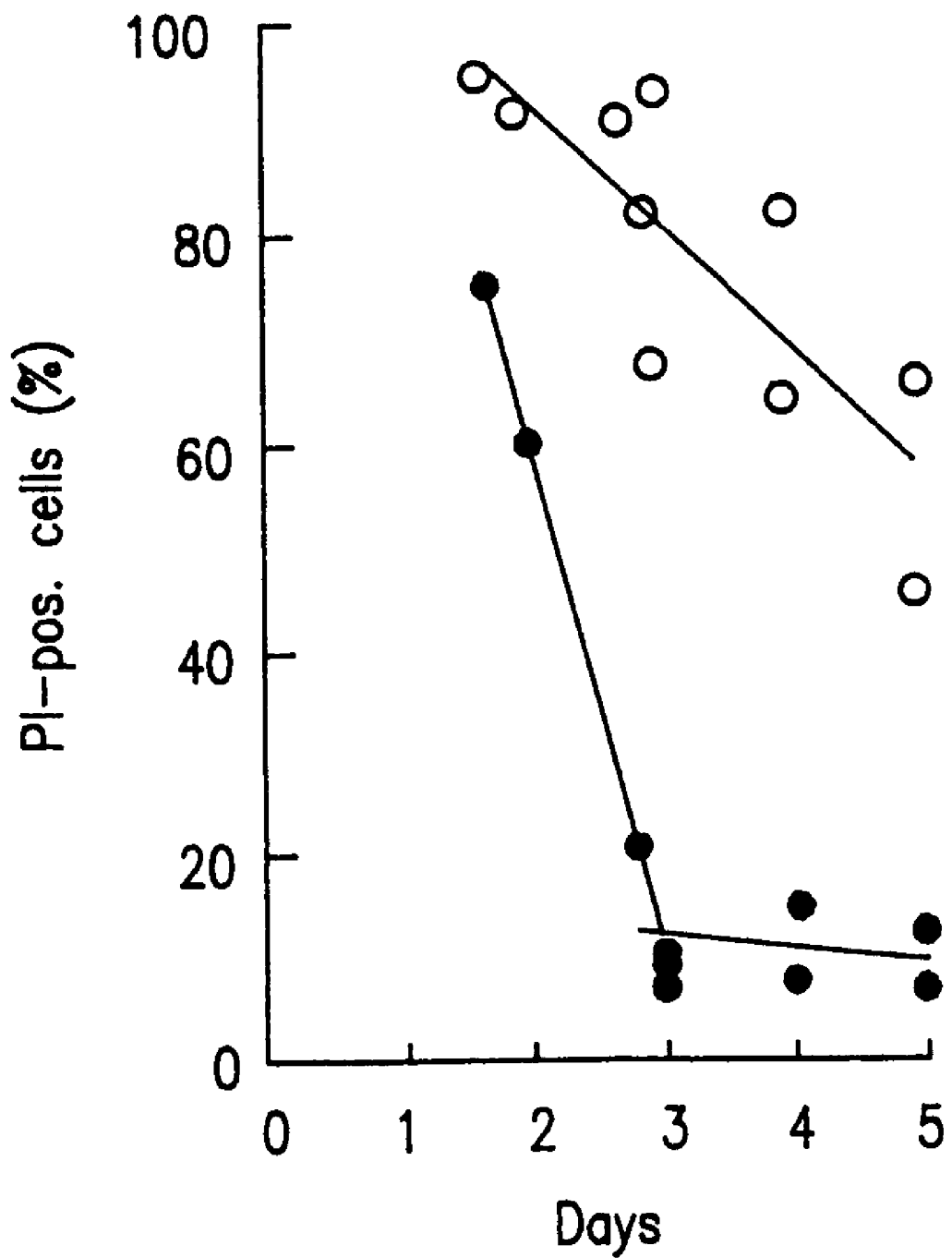
Figure 10:
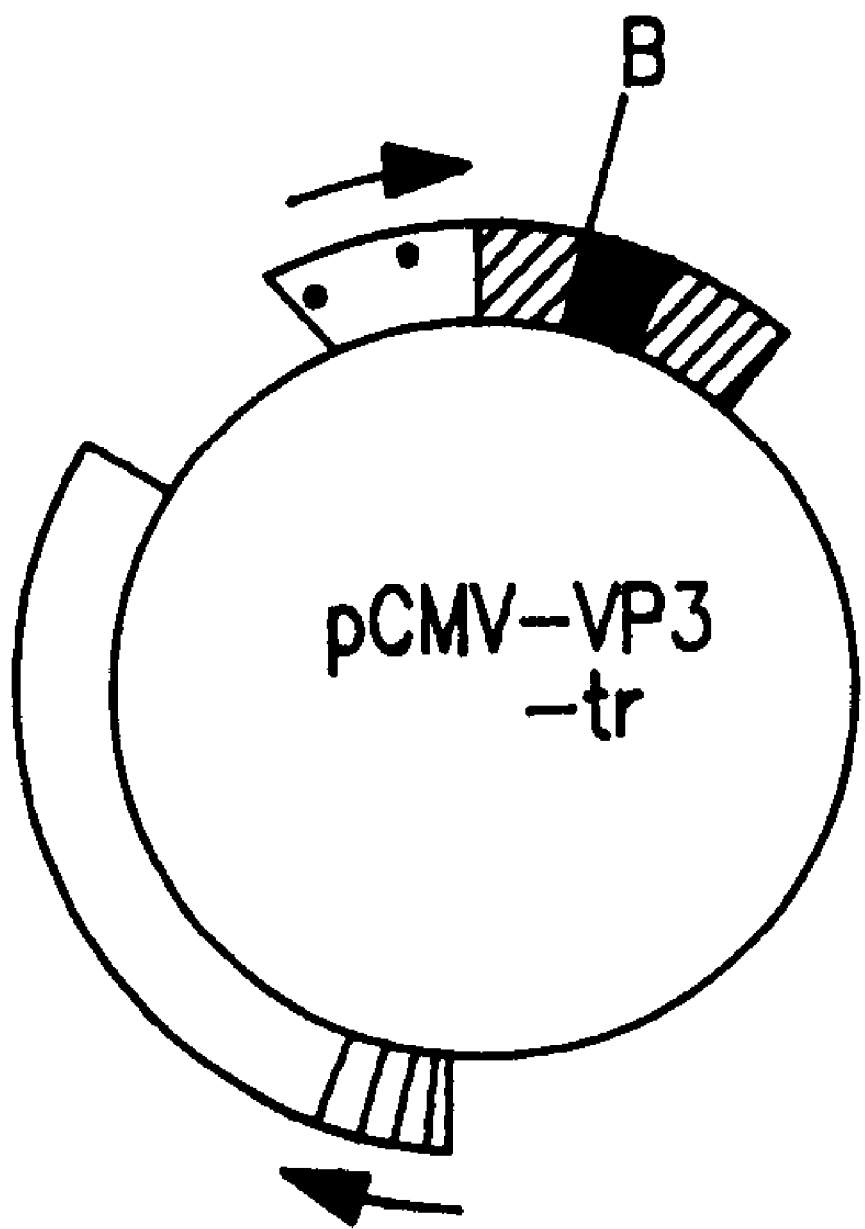
Figure 11A:
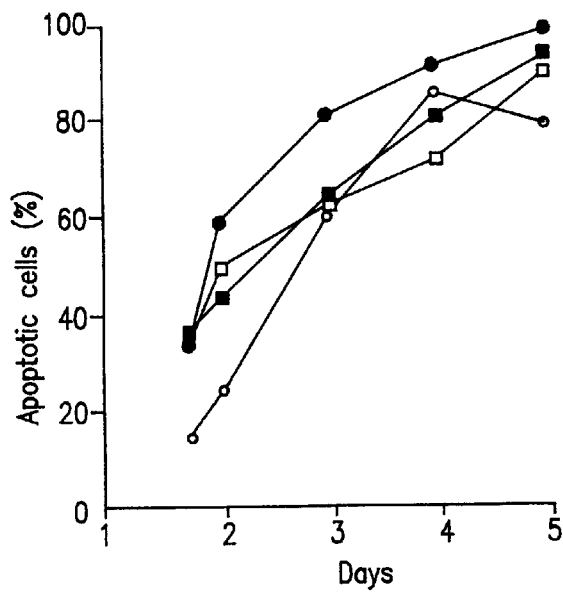
Figure 11B:
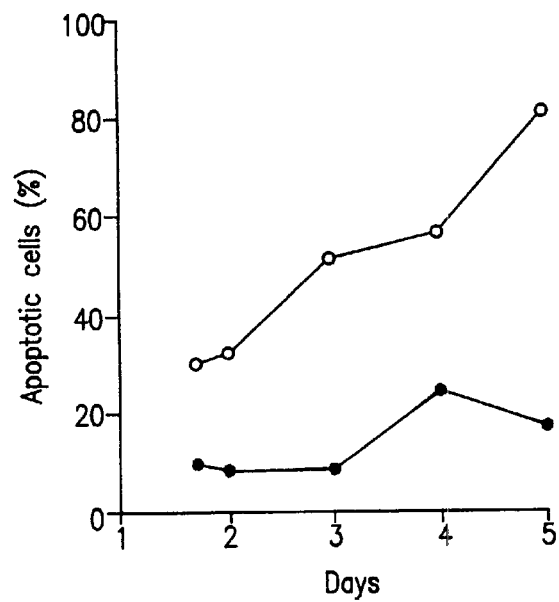
Figure 12A:
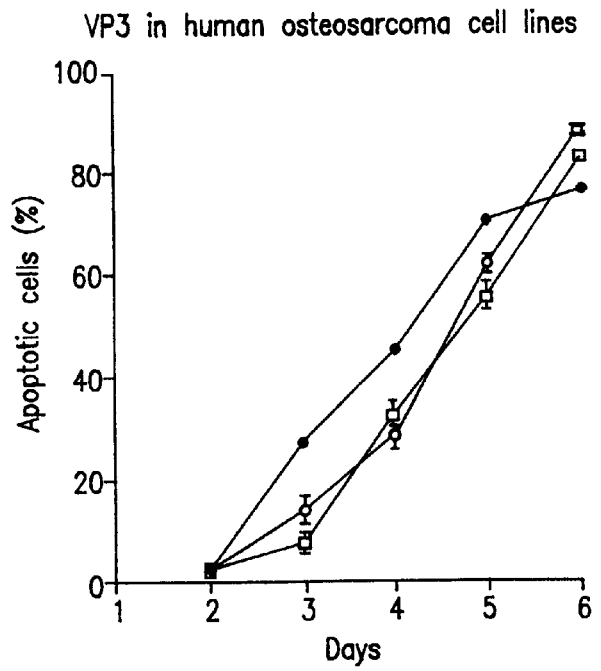
Figure 12B:
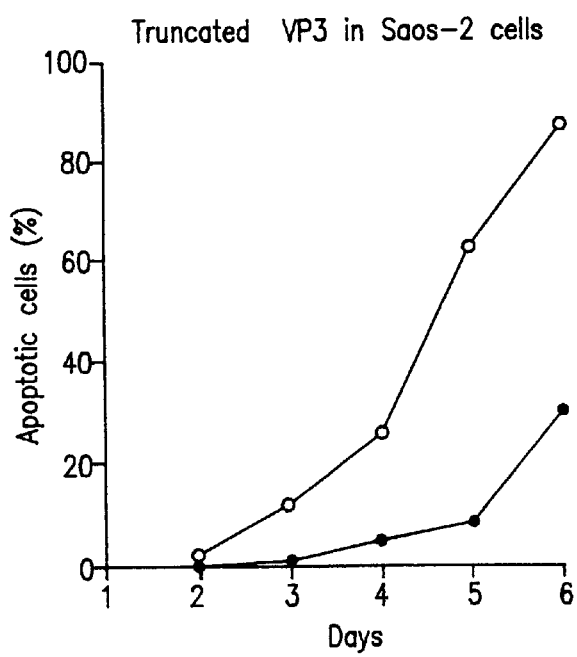

In a pepscan analysis (Geysen et al., (1984) Proc. Nat'l. Acad. Sci. (USA) 82:1978–1982) the epitope of the monoclonal antibody 111.2 was localized in the middle of VP2 (FIG. 6). The monoclonal antibody 111.3 was found to be directed against an epitope at the N terminal end of VP3 (FIG. 7), namely beside the VP3 epitope recognized by the monoclonal antibodies CVI-CAV-85.1 (FIG. 5).

CAV challenge experiments

Materials antibodies protect young chicks against clinical symptoms caused by a CAV infection. We have studied which group(s) of chickens immunized with specific recombinant CAV proteins became offspring protected against CAV challenge.

Groups of between 23 and 35 day-old offspring were challenged with a high doses of CAV. Six days after infection virus was isolated and the animals evaluated for clinical symptoms characteristic of CAV; atrophy of the thymus, decreased hematocrit and increased mortality. Five animals which were subjected to section and which had mother animals injected with PBS buffer, were all found to have a macroscopically visibly reduced thymus. In case of offspring of mother animals injected with recombinant VP2+VP3, four of the five animals had a small thymus. However, the five offspring, subjected to section, of mother animals injected with the three recombinant CAV proteins together were all found to have a normal thymus. In the group of offspring of mother animals treated with VP1+VP2 only one of the five animals examined was found to have a reduced thymus (Table 4).

Fourteen days after infection, again five animals per group were subjected to section. All offspring of mother animals immunized with recombinant VP2+VP3 or PBS buffer suffered from thymus atrophy. The examined offspring of the group of animals injected with the three recombinant CAV proteins together were all found to have normal thymuses. Only one of the five examined chicks of the animals injected with recombinant VP1+VP2 was found to have a reduced thymus (Table 4). An independent experiment showed that offspring of mother animals injected with recombinant VP1 and VP3 had reduced thymuses, as described for the offspring of mother animals injected with recombinant VP2 and VP3 (Koch, results not published).

TABLE 4

Section Findings after CAV Challenge in Offspring of Mother Animals Immunized with Recombinant CAV Products

| Group 1<br>VP1 + VP2 + VP3 | Group 2<br>VP1 + VP2 | Group 3<br>VP2 + VP3 | Group 4<br>PBS |
| --- | --- | --- | --- |
| 0/5[#] | 1/5 | day 6 after infection<br>4/5 | 5/5 |
| 0/5 | 1/5 | day 14 after infection<br>5/5 | 5/5 |
| 1/3 | 0/0 | more than 14 days after infection<br>13/14 | 6/6 |
| (ND: (2/2)[&]) | | (ND: 1/14) | |

[#]Number of animals with small thymus.
[&]No section performed because of a specific mortality.

Fourteen days after infection the hematocrit of all CAV infected offspring was determined. A hematocrit of 27% was selected as the limit for anemia. The offspring of the mother animals injected with PBS buffer were all found to have a strongly reduced hematocrit, with values varying between 7 and 19% (Table 5). Offspring of the mother animals injected with recombinant VP2+VP3 have a slightly higher hematocrit on average. In these groups only a single animal had a hematocrit higher than 27. An independent experiment showed that also offspring of mother animals injected with recombinant VP1 and VP3 had a reduced hematocrit. Of the 35 examined offspring of the animals injected with preparations containing VP1, VP2 and VP3, only one animal had a deviating hematocrit, whereas in the VP1+VP2 group, two of the 29 examined animals had a hematocrit below 27%.

TABLE 5

Hematocrit values in offspring of mother animals immunized with combinations of recombinant-CAV baculo products

| VP1 + VP2 + VP3 | VP1 + VP2 | VP2 + VF3 | PBS |
| --- | --- | --- | --- |
| 37[i] | 29 | 14 | 18 |
| 30 | 31 | 20 | 11 |
| 33 | 34 | 13 | 16 |
| 33 | 30 | 28 | 15 |
| 34 | 35 | 25 | 19 |
| 28 | 34 | 8 | 13 |
| 34 | 22 | 28 | 9 |
| 32 | 34 | 12 | 11 |
| 29 | 36 | 6 | 17 |
| 30 | 37 | 7 | 14 |
| 29 | 32 | 18 | 10 |
| 36 | 30 | 16 | 17 |
| 31 | 25 | 19 | 18 |
| 32 | 36 | 14 | |
| 28 | 34 | 29 | 8 |
| 32 | 33 | 13 | 10 |

TABLE 5-continued

Hematocrit values in offspring of mother animals immunized
with combinations of recombinant-CAV baculo products

| | VP1 + VP2 + VP3 | VP1 + VP2 | VP2 + VF3 | PBS |
|---|---|---|---|---|
| | 33 | 32 | 8 | 8 |
| | 31 | 36 | 31 | 12 |
| | 37 | 34 | 14 | 14 |
| | 32 | 28 | 25 | 9 |
| | 38 | 32 | 19 | 11 |
| | 30 | 35 | 15 | 8 |
| | 33 | 36 | 7 | 12 |
| | 23 | | 17 | 17 |
| | 38 | | 14 | 12 |
| | 37 | | 9 | 13 |
| | 31 | | 18 | |
| | 32 | | 8 | |
| | 29 | | 12 | |
| | 32 | | 14 | |
| | 32 | | | |
| | 31 | | | |
| | 32 | | | |
| | 34 | | | |
| | 32 | | | |
| average: | 32.1 | 32.4 | 16.0 | 12.7 |
| stand. dev. | 3.09 | 3.66 | 6.98 | 3.52 |
| max-min. | 23–38 | 22–37 | 6–28 | 3,52 |
| number | n = 35 | n = 23 | n = 30 | n = 26 |

[1]Hematocrit in individual animal.

A high mortality rate was observed with offspring of mother animals injected with recombinant VP2 and VP3, 50.9% and with PBS, 48.3%. In the group of offspring of mother animals injected with recombinant VP1+VP2+VP3 the mortality is 9% and with VP1+VP2 15.4%. However, most of the animals died within five days after challenge. The mortality caused by a CAV infection is generally somewhat later. For this reason we have distinguished in Table 6 between mortality before day 14 and after day 14 after challenge. The mortality before day 14 is often aspecific, inter alia as a result of injection. The mortality after day 14 is in the group of animals with maternal antibodies against VP1+Vp2+VP3, 7%; against VP1+VP2, 0%, Vp2+VP3, 27.4% and in the control group 20.7%. In the VP2+VP3 group, 8 animals died after taking blood samples for determining the hematocrit as a result of the poor condition of the chicks, most probably caused by the anemia. In the PBS group, two animals died during blood taking. All these animals had a clearly reduced thymus.

TABLE 6

Mortality After CAV Challenge in Offspring of
Mother Animals Immunized Recombinant CAV Products

| Group 1<br>VP1 + VP2 + VP3 | Group 2<br>VP1 + VP2 | Group 3<br>VP2 + VP3 | Group 4<br>PBS |
|---|---|---|---|
| 1/43<br>(2%) | 7/39<br>(15.4%) | before day 14<br>after injection<br>12/51<br>(23.5%) | 8/29<br>(27.6%) |
| 3/43<br>(7%) | 0/39 | after day 14<br>after injection<br>14/51<br>(27.4%) | 6/29<br>20/7% |

The viremia in the CAV infected offspring was examined by carrying out a virus isolation on blood cells. Heparin blood samples of five animals per group were taken on 6 and 14 days after challenge. The offspring of mother animals injected with VP2+VP3 or PBS, and which had practically no protection against CAV infections, were found to contain relatively high virus titers 6 and 14 days after infection. Six days after infection the offspring of animals injected with VP1+VP2+VP3 or VP1+VP2 were found to contain a clearly lower virus titer than the above-mentioned offspring. Fourteen days after infection only the group of offspring of animals injected with VP1+VP2+VP3 had a clearly lower virus titer than the other three groups.

The results of the induction of neutralizing antibodies in mother animals show that the recombinant CAV proteins VP1 and VP2 are very important for the induction of a neutralizing immune response. The infection experiments show that the recombinant CAV protein VP3 gives a supplementary protection in addition to the effect obtained by VP1+VP2. Fertilized eggs of the five groups of immunized hens were hatched. The chicks were injected intramuscularly on day 1 with $10^{5.5}$ TCID$_{50}$ CAV-Cux-1. On 6 and 14 days after infection 5 chickens per group were subjected to section. The thymus was analyzed macroscopically and immunohistologically. Also, heparin blood was taken, and the blood cells were tested in a virus reisolation assay. Fourteen days after infection heparin blood was collected from all animals to determine the hematocrit.

Example 5

Immunohistology and immunofluorescence

Frozen coupes of thymus and bone marrow were made and used for immunoperoxidase staining with CAV-specific monoclonal antibodies, as described by Jeurissen et al. (1988) Vet. Immunol. Immunopathol. 19:225–238) Cells were fixed with 80% acetone and used for immunofluorescence tests with CAV-specific monoclonal antibodies and goat anti-mouse IgC conjugated with fluorescein isothiocyanate (Noteborn et al. (1990)

Immunofluorescence showed that monoclonal antibodies directed against VP2 and VP3 recognize specific structures in CAV infected MDCC-MSB1 cells. None of the monoclonal antibodies directed against CAV antigens reacted with uninfected MDCC-MSB1 cells. The VP2-specific monoclonal antibodies recognize other structures than VP3 specific monoclonal antibodies in CAV infected cells.

Detection of CAV in blood samples

Blood samples of CAV infected chicks were washed thrice with PBS and taken up in 1 ml. Twenty microliters of the cell suspension obtained were added to $10^5$ MDCC-MSB1 cells. The MDCC-MSB1 cells were 10 times diluted every 4–5 days, transferred to fresh culture medium, until a CAV-specific cytopathogenic effect became visible. If after 10 passages no cytopathogenic effect could be observed yet, then the virus isolation was considered to be negative. The number of times of passage is a measure for the amount of infectious CAV present in the blood of the infected chicks.

Example 6

Simultaneous Expression of Recombinant VP1 and VP2

Construction of a Recombinant-VP1/VP2 Transfer Vector

Figure 13:
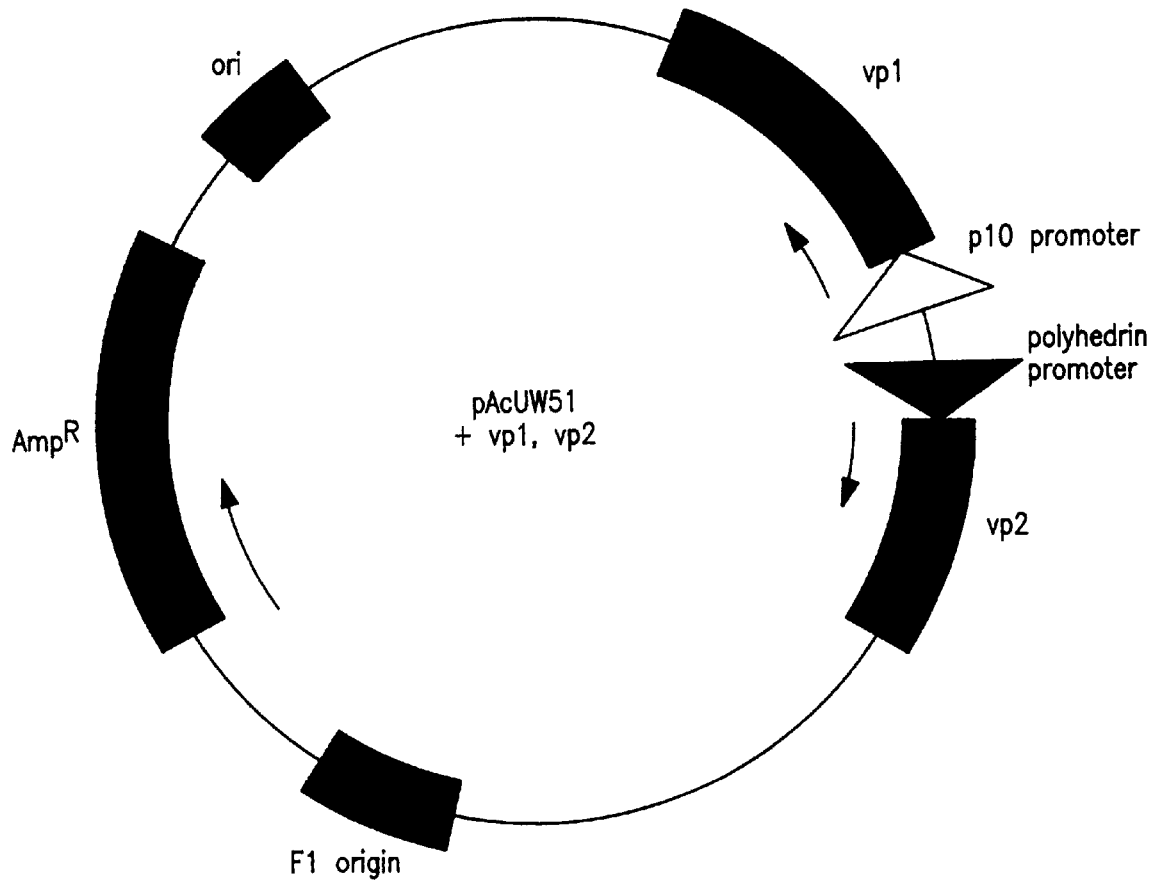

The coding sequences for the CAV proteins VP1 and VP2 were cloned into the baculovirus transfer vector pAcUW51 (cat. no: 21205P), which was commercially obtained from PharMingen, San Diego, USA. This vector is shown in FIG. 13 and contains the polyhedrin flanking region, within their midst the baculovirus polyhedrin promoter and the p10 promoter and for both transcription units, the required 3'-non-coding transcriptional sequences including the polyadenylation signals. The transfer vector contains prokaryotic sequences for multiplication in bacteria.

Figures 14A, 14B:
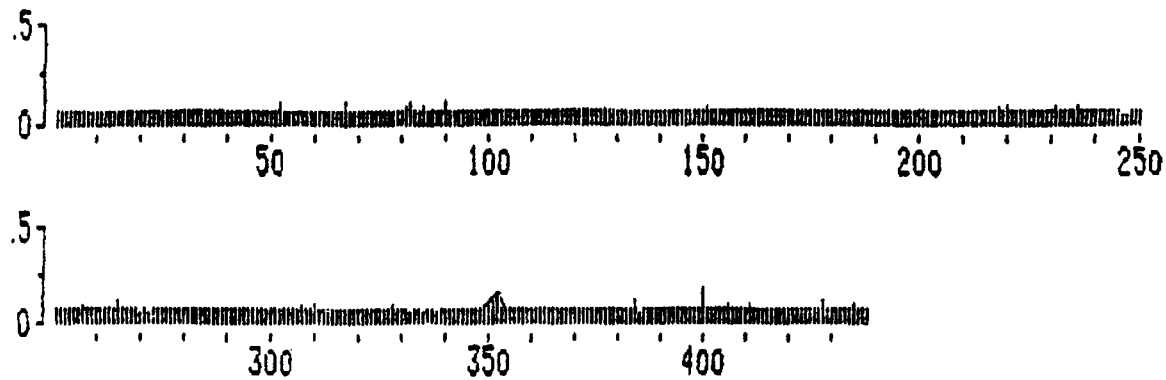
Figures 15A, 15B:
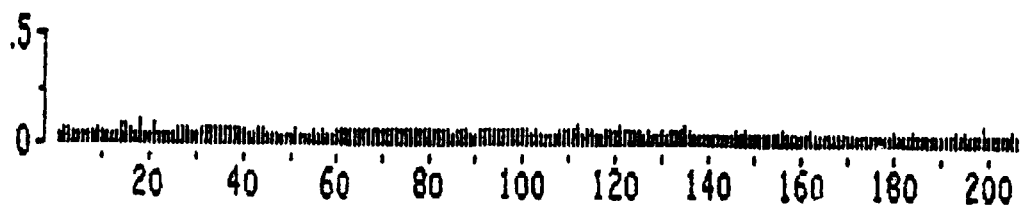

The plasmid pET-16b-VP2 contains CAV DNA sequences of positions 380 to 1512. This CAV DNA fragment contains the coding region for VP2 flanked by 484 bp 3'-non-coding CAV DNA sequences. 106 bp downstream of the start codon for VP2 the start condon for VP3 is found in another reading frame. The plasmid pET-16b-VP2 was treated with the restriction enzymes NdeI and NheI, and the sticky ends were filled by means of Klenow polymerase. A 0.8 kb CAV DNA fragment was isolated. The plasmid pAcUW51 was linearized with BamH1, the stick ends filled by means of Klenow polymerase and finally treated with alkaline phosphatase (CIP). The 0.8 kB CAV DNA fragment was ligated at the linearized pAcUW51 DNA. The orientation of VP2 in pAcUW51 was determined by restriction enzyme analysis. This construct was called pUW-VP2.

The plasmid pET-16b-VP1 contains CAV DNA sequences of positions 853 to 2319. The CAV DNA insertion contains the complete coding region for the protein VP1 flanked by 117 bp 3'-non-coding CAV DNA sequences. The plasmid pET-16b-VP1 was treated with the restriction enzymes NdeI and EcoRI, and the sticky ends were filled by means of Klenow polymerase. A 1.45 kb CAV DNA fragment was isolated. The plasmid pUW-VP2 was linearized by EcoRI, the sticky ends filled by means of Klenow polymerase and finally treated by CIP. The 1.45 kb CAV DNA fragment was ligated at the linearized pUW-VP2. The orientation of VP1 opposite of the p10 promoter unit was determined by restriction-enzyme analysis, and the final construct pAcVP1/VP2 is shown in FIG. 1.

Construction of recombinant-VP1/VP2 baculovirus

Recombinant transfer vector pAcVP1/VP2 DNA was transfected with linearized recombinant baculovirus AcRP23-lacZ DNA, in sf9 cells. After homologous recombination baculoviruses were obtained, which had incorporated in the polyhedrin unit instead of the lacZ the two CAV proteins VP1 and VP2 under regulation of the promoter of the p10 or polyhedrin gene, respectively. In first instance, the recombinant CAV viruses were characterized for the absence of B-galactosidase activity in plaques of baculovirus-infected insect cells. Further the integration of CAV DNA sequences in the baculovirus genome was determined by means of a CAV-specific DNA probe in a hybridization experiment.

Expression of the CAV proteins VP1 and VP2 in sf9 cells

The simultaneous expression of the CAV proteins VP1 and VP2 in sf9 cells infected with recombinant-VP1/VP2 baculovirus was analyzed by Coomassie-brilliant blue staining and protein labeling with Promix (ICN, USA) or $^{3}$H-leucine (Amersham, UK) and PAA-SDS gel electrophoresis.

As described above, lysates of insect cells infected with recombinant-VP1 vaculovirus contained a CAV-specific protein of 52 kD and expreswsion of VP2 by recombinant-VP2 baculovirus in infected insect cells produced a major specific product of 30 kDa. Infection of insect cells with recombinant-VP1/VP2 baculovirus resulted in the synthesis of both the CAV-specific proteins of 52 kD and 30 kD. Both CAV-specific products could be detected as radioactively labeled protein band or Coomassie-brilliant blue stained protein band. The latter result indicates that both products are produced in relatively high levels in recombinant-VP1/VP2-baculovirus-infected insect cells. sf9 cells infected with a recombinant-lacZ baculovirus did not contain these CAV-specific proteins.

As expected, we have obtained evidence that inoculation in hens with crude lysates of recombinant-VP1/VP2-infected sf9 cells induces neutralizing antibodies directed against CAV.

The production and characterization of neutralizing monoclonal antibodies against CAV Two types of CAV-specific monoclonal antibodies are described above. One type is directed against VP2, while the other is directed against VP3. Neither of these types of monoclonal antibodies reveal a CAV-specific neutralizing activity. Even more important was that none of these monoclonal antibodies was directed against VP1. We assumed that a neutralizing monoclonal antibody might be directed against VP1, for the capsids contain mainly VP1 (Todd et al, (1990) G. Gen Virol. 71:819–823). Below, we describe the production of neutralizing antibodies against CAV.

For the production of neutralizing monoclonal antibodies against CAV, mice were injected with purified CAV particles. The supernatant of a 1 liter culture of CAV-infected MDCC-MSB1 cells was concentrated forty fold by means of a MILLITAN 300-kDa filter (Millipore, USA). The supernatant was dialyzed against 10 nM Tris(ph 8.7)-1 mM EDTA (TE) buffer. Subsequently, sodium dodecyl sulphate (SDS) (0.5% final concentration) was added to the CAV-capsid suspension and incubated for 30 minutes at 37° C. Finally, the CAV capsids were pelleted on a 30% sucrose cushion. The pellet containing the CAV capsids was resuspended in 1 ml TE buffer. Mice were twice injected with 100 μl CAV-capsid suspension.

As a first screening for (neutralizing) monoclonal antibodies against CAV, microtitre wells were coated with recombinant-VP1/VP2-baculovirus infected insect cells, which co-synthesized both VP1 and VP2. CAV-specific antisera with a high neutralizing titer reacted at a dilution of 1:1000 specifically with the recombinant VP1 and/or VP2 products (see below). Several different hybridoma cell lines producing monoclonal antibodies, which specifically reacted with recombinant VP1/VP2 products, were obtained.

A CAV-specific serum neutralization test, carried out as described above, showed that three of these monoclonal antibodies obtained, had a neutralizing activity against CAV. These three CAV-specific neutralizing monoclonal antibodies were called 132.1; 132.2 and 132.3. Immunofluorescence showed that the three neutralizing monoclonal antibodies 132.1, 132.2 and 132.3 recognize specific structures in CAV-infected MDCC-MSB1 cells. None of these monoclonal antibodies reacted with uninfected MDCC-MSB1 cells.

Electron-microscopic analysis was carried out with purified CAV particles incubated with neutralizing antibodies against CAV (132.1) or with monoclonal antibodies 111.1 (against VP2) or 111.3 (against VP3). The various monoclonal antibodies were detected by immunogold labeling. Only the neutralizing monoclonal antibodies 132.1 were found to bind to CAV particles. Binding of the monoclonal antibody 132.1 to a CAV particle resulted in its lysis. Furthermore, CAV capsids, which were lysed due to incubation with the neutralizing monoclonal antibody 132.1, showed no binding with monoclonal antibodies directed against VP2 or VP3.

These results reveal the mechanism by which the neutralizing monoclonal antibodies act: they cause the lysis of the virus capsids, by doing so causing non-infectious particles. Furthermore, these data suggest that purified CAV particles contain (almost) only VP1.

Pepscan analysis (Gheysen et al., (1984) *Proc. Nat'l Acad Sci.* (USA) (82:178–182) revealed that none of the three neutralizing monoclonal antibodies reacted significantly with one of the 12-mers derived from VP1 or VP2. For the sake of brevity only the data obtained with monoclonal antibody 132.1 are shown for VP1 in FIG. 14, and for VP2 in FIG. 15. These results indicate that the neutralizing monoclonal antibodies are directed against a conformational epitope. These data were confirmed by the following experiments. Purified CAV particles, dotted on a nylon filter under native conditions, still could react with the neutralizing monoclonal antibody 132.1. However, after boiling in the presence of SDS, the CAV capsid proteins did not bind to monoclonal antibody 132.1.

Immunoprecipitations experiments, carried under native conditions, as described by Noteborn et al., In: Virus Diseases of Poultry-New and Evolving Pathogens, (1994) 195–212, with partially purified CAV particles and monoclonal antibody 132.1, 132.2 or 132.3 showed that a protein of about 50 kDa was precipitated by these monoclonal antibodies. These results indicate that the neutralizing monoclonal antibodies are directed against VP1.

The role of VP2 for the formation of the neutralizing epitope of VP1

As reported above, simultaneous synthesis and not simply mixing of recombinant CAV proteins VP1 and VP2 is required to obtain a neutralizing and protective immune response suggests that VP2 is a non-structural protein that at some stage of infection is required for virus assembly and/or the correct conformation of VP1, which result(s) in the formation of the neutralizing epitope(s). One explanation of the requirement of VP2 might be that it acts as a scaffold protein that is necessary during the assembly of the virion but absent in the final product. Examples of scaffold proteins are the IVa2 and 39kDa proteins of adenovirus (D'Halluin et al., (1978) J. Viral. 26:357–363: Persson et al., (1979) Virology 93:198–208. These proteins act as scaffolds for the formation of the so-called light capsid, but are removed in the next step. VP2 might function in a similar way during the formation of CAV virions. However, at this stage, we cannot entirely exclude that (very) small amounts of VP2 that remained undetected in electroblots of purified CAV preparations or in electron microscopic photographs of lysed CAV particles incubated with immunogold-labeled VP2-specific monoclonal antibodies, as described above, associate with VP1 and form conformational neutralizing epitopes. Recently, evidence for the presence of VP2 in gradient-purified CAV was reported (Buchholdz, (1994) Charakterisierung des Hühneranämievirus (CAV mit hilfe von monoklonal antikörpern. Dissertation Free University of Berlin, 1994, Journal no 1738, Berlin, Germany.

In the following experiments, evidence is provided that the neutralizing epitope of VP1 is only (optimal) present, when VP2 is simultaneously synthesized. Insect cells were infected with recombinant-CAV baculoviruses expressing VP1, VP2 (PCT/NL94/00168) or both VP1 plus VP2. The infected sf9 cells were harvested 3 or 4 days after infection and fixed with 80% acetone and used for immunofluorescence tests with the CAV-specific neutralizing monoclonal antibody 132.1 and goat anti-mouse IgC conjugated with fluorescein isothiocyanate (Noteborn et al., (1990). The cells containing only the CAV-specific protein VP2 did not react at all with the monoclonal antibody 132.1. Cells containing only VP1 revealed a very poor immunofluorescence signal after incubation with monoclonal antibody 132.1. However, insect cells infected with recombinant-VP1/VP2 baculovirus expressing both VP1 and VP2 bound very strongly to the neutralizing monoclonal 132.1. PAA-SDS gel electrophoresis of in parallel radioactive-labeled lysates of insect cells expressing VP1, VP2 or VP1 plus VP2, revealed that VP1 is expressed at the same level when expressed only or simultaneously with VP2.

In conclusion, the neutralizing epitope of VP1 is only formed when VP2 is present. This implies that VP1 and VP2 associate with each other during a short time period. By means of immunoprecipitations under very mild conditions, we have examined whether VP1 could associate with VP2. sf9 insect cells were infected with recombinant baculoviruses, which synthesized VP1, VP2, or VP1 plus VP2. Two days after infection, the cells were incubated with Promix label (ICN, USA) and four hours later, the cells were lysed in E1A buffer (50 nM Tris (pH7.5), 0.1% Triton X-100, 250 mM NaCl, 50 mM NaF, and 5 mM EDTA) and incubated with monoclonal antibody 111.1 directed against VP2 for two hours at 4° C., washed with B1A buffer and separated on a PAA-SDS gel. The results clearly reveal that monoclonal antibody 111.1 precipates VP2 when VP2 is synthesized alone or in the presence of VP1. In the case that besides VP2, VP1 was expressed also, VP1 co-precipitated to a small extent with VP2. The monoclonal antibody 111.1 did not detectably precipitate VP1, when VP1 was synthesized in the absence of VP2. These data indicate that VP1 and VP2 are (to a relatively small amount) associated to each other. During this association event, VP1 might obtain its conformation resulting in the neutralizing epitope.

Basis for the development of vaccines against CAV infections

The above presented results together with those described in PCT/NL94/00168 show that for the induction of neutralizing antibodies against CAV, VP1 is needed to have a specific conformation. In a baculovirus expression system, this correct VP1 confirmation is only possible, when VP1 plus VP2 or VP1 plus VP2 plus VP3 are simultaneously synthesized.

The recombinant CAV products, VP1 plus VP2 or VP1 plus VP2 plus VP3, which will be used for vaccination of laying-hens, can be synthesized by means of the baculovirus system. The CAV proteins can also be synthesized by means of other expression systems, such as yeast cells, via (retro)-viral infection or gene amplification (CHO-dhfr system) in mammalian cell systems.

In principle, the expression of fragments of VP1 (in combination with VP2 or VP2 and VP3) may be sufficient for the induction of a protective immune response. The fact that 12-mers of VP1 can not react with neutralizing antibodies against CAV indicates that larger VP1 fragments are needed for getting the correct VP1 conformation to form the neutralizing epitope. However, one should take into account that minor amino-acid mutations or a few amino-acid deletions might not influence the formation of the neutralizing epitope of VP1.

That fact that two or three proteins encoded by the CAV open reading frames can induce a protective immune response is also applicable to the development of living virus vectors. The coding sequences for VP1 plus VP2 or VP1 plus VP2 plus VP3 are then cloned into living virus vectors.

It is also possible that one of the CAV proteins, VP1, VP2 or VP3, separately, but then within the context of a living virus vector, is also suitable for the induction of a protective immune response against CAV infections. The expression of fragments of one of the above-mentioned CAV proteins by living virus vectors may be sufficient for the induction of a protective immune response.

The fact that VP3 causes apoptosis in, i.e., chicken mononuclear cells (PCT/NL94/00168) makes it preferable to prepare living virus vectors not expressing VP3. The replication of i.e., Marek virus might be negatively influenced by VP3-induced apoptosis. Alternatively, one can construct living virus vectors expressing VP1, VP2 and a truncated VP3 lacking the C-terminal 11 amino acids which cause strong induction of apoptosis by VP3.

Enzyme-linked immunosorbens assay (ELISA) based on a neutralizing antibody against CAV A complex-trapping-blocking (CTB)-ELISA has been constructed using enriched CAV particles derived from CAV-infected MDCC-MSB-1 cells or recombinant VP1/VP2 proteins synthesized by means of the above described baculovirus system.

Microtiter wells (Greiner, FRG) were coated with the CAV-specific neutralizing monoclonal antibody 132.1, which was 1:10,000 diluted in 50 nM sodium bicarbonate pH 9.6. Wash the wells three times with tap water containing 0.5% Tween 80. Saturate the wells with 100 μl phosphate-buffered saline containing 4% horse serum, 51 gram/liter NaCl, and 0.05% Tween 80. Next, 50 μl of non-diluted chicken serum and 50 μl of thirty times concentrated supernatant containing CAV particles, or 50 μl of a lysate of insect cells containing recombinant 1 and VP2 proteins, were mixed, added per well and incubated for 1 hour at 37° C. The wells were washed three times with tap water containing 0.05% Tween 80. 100 μl of a standard solution of tetramethylbenzidine, sodium acetate and hydrogen peroxide was added to the wells and incubated for 10 minutes at room temperature. The reactions were blocked with 10% $H_2SO_4$. The various wells were examined at 450 nm, as standard.

Serum from CAV-infected chickens contains antibodies which will block all epitopes on the CAV capsids or recombinant VP1/VP2. This means that the CAV capsid or recombinant VP1/VP2 will not bind to the coated monoclonal antibody 132.1. Negative serum, however, will allow binding of CAV capsids or recombinant VP1/VP2 to the coated 132.1. A signal smaller than 0.5 of the signal detected with a negative control serum will be examined as positive.

The detection level of our CTB-ELISA are titers of $2^4$ to $2^5$ as determined in a serum neutralization test, which is very sensitive. More than 400 sera were analyzed. Comparison to the serum neutralization test revealed that 96.5% of the positive sera within the serum neutralization test were positive within the CTB-ELISA, and 98.3% of the negative sera within the serum neutralization test were negative within the CTB-ELISA.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. An attenuated Chicken Anemia Virus comprising a mutation in a nucleotide sequence coding for a Chicken Anemia Virus polypeptide selected from the group consisting of VP2 and VP3, wherein said mutation decreases the apoptosis induced by said attenuated Chicken Anemia Virus.

2. An attenuated Chicken Anemia Virus according to claim 1, wherein said Chicken Anemia Virus expresses a Chicken Anemia Virus VP3 polypeptide comprising an amino acid sequence depicted in amino acid residues 1 through 110 SEQ ID NO: 7.

3. The attenuated Chicken Anemia Virus according to claim 1, wherein said Chicken Anemia Virus polypeptide is VP3.

4. The attenuated Chicken Anemia Virus according to claim 1, wherein said mutation is in a nucleotide sequence encoding amino acid residues 111 through 121 of an amino acid sequence depicted in SEQ ID NO: 7.

5. The attenuated Chicken Anemia Virus according to claim 1, wherein said nucleotide sequence encodes a polypeptide which comprises amino acid residues 1 through 110 of an amino acid sequence depicted in SEQ ID NO: 7.

* * * * *

UNITED STATES PATENT AND TRADEMARK OFFICE
CERTIFICATE OF CORRECTION

PATENT NO. : 5,922,600
DATED : 13 July, 1999
INVENTOR(S) : M.H.M. Noteborn and G. Koch It is certified that error appears in the above-identified patent and that said Letters Patent is hereby corrected as shown below:

In the Inventors section [75], "Matheus" should be --Mathieu--.

In the References Cited section [56], 2nd column, line 5, "immunodeficeincy" should be --immunodeficiency--.

In the Other Publications section, page 2, 1st column, line 5, "Ehcracterization" should be --Characterization--.

In column 1, line 32, "order" should be --older--; line 50, "Tn:" should be --In:--.
In column 2, line 17, "AN" should be --an--.
In column 3, line 44, "VO3tr" should be --VP3tr--.
In column 5, line 18, "be" should be --by--.
In column 6, line 29, "immuneassays" should be --immunoassays--.
In column 7, line 17, "CAB" should be --CAV--;
  lines 57-58, "Moleculara Clong" should be --Molecular Cloning--.
In column 8, line 13, "Gene$^2$" should be --Gene--.
In column 9, line 57, "32P" should be --$^{32}$P--; line 61 "3H" should be --$^3$H--.
In column 10, line 12, "mio" should be --moi--.
In column 11, line 35, "Recomibinant Vp1" should be --Recombinant VP1--;
  line 60, "member" should be --number--.
In column 12, line 12, "FReund's" should be --Freund's--;
  line 25, "CBS" should be --PBS--;
  line 40, "Recomibinant Vp1" should be --Recombinant VP1--;
  line 64, "member" should be --number--.
In column 13, line 35, "2x107" should be --$2 \times 10^7$--;
  lines 45, 46, 48 and 56, "VPI" should be --VP1--.

UNITED STATES PATENT AND TRADEMARK OFFICE
CERTIFICATE OF CORRECTION

PATENT NO. : 5,922,600
DATED : 13 July, 1999
INVENTOR(S) : M.H.M. Noteborn and G. Koch It is certified that error appears in the above-identified patent and that said Letters Patent is hereby corrected as shown below:

In column 15, line 23, "$10^4$-$10_5$" should be --$10^4$-$10^5$--.
In column 16, line 53, "VP2 + VF3" should be --VP2 + VP3--;
 line 64, "[where no number appears in the column under PBS]" should be --7--.
In column 17, line 6, "VP2 + VF3" should be --VP2 + VP3--;
 line 25, "6-28" should be --6-31--, and "3,52" should be --7-19--;
 lines 40-41, "Vp2" should be --VP2--;
 line 59, "20/7%" should be --20.7%--.
In column 18, line 34, "IgC" should be --IgC--.
In column 19, line 39, "B-galactosidase" should be --β-galactosidase--.
In column 20, line 11, "G. Gen Virol." should be --J. Gen. Virol.--;
 line 18, "ph" should be --pH--.
In column 21, line 10, "Immunoprecipitations" should be --Immunoprecipitation--;
 line 55, "IgC" should be --IgG--.
In column 22, line 13, "B1A" should be --E1A--.

Signed and Sealed this

Twenty-fourth Day of April, 2001

*Attest:*

NICHOLAS P. GODICI

*Attesting Officer*    *Acting Director of the United States Patent and Trademark Office*

```
                              SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
          (A) LENGTH: 16 base pairs
          (B) TYPE: nucleic acid
          (C) STRANDEDNESS: unknown
          (D) TOPOLOGY: unknown (ii) MOLECULE TYPE: DNA (genomic)

(iii) HYPOTHETICAL: NO (xi) SEQUENCE DESCRIPTION: SEQ ID NO:1:

GATCCAACCC GGGTTG                                                          16

(2) INFORMATION FOR SEQ ID NO:2:

(i) SEQUENCE CHARACTERISTICS:
          (A) LENGTH: 16 base pairs
          (B) TYPE: nucleic acid
          (C) STRANDEDNESS: unknown
          (D) TOPOLOGY: unknown (ii) MOLECULE TYPE: DNA (genomic)

(iii) HYPOTHETICAL: NO (xi) SEQUENCE DESCRIPTION: SEQ ID NO:2:

AATTCAACCC GGGTTG                                                          16

(2) INFORMATION FOR SEQ ID NO:3:
```

(i) SEQUENCE CHARACTERISTICS:
    (A) LENGTH: 449 amino acids
    (B) TYPE: amino acid
    (C) STRANDEDNESS: unknown
    (D) TOPOLOGY: unknown (ii) MOLECULE TYPE: protein (iii) HYPOTHETICAL: NO (xi) SEQUENCE DESCRIPTION: SEQ ID NO:3:

```
Met Ala Arg Arg Ala Arg Arg Pro Arg Gly Arg Phe Tyr Ser Phe Arg
1               5                   10                  15

Arg Gly Arg Trp His His Leu Lys Arg Leu Arg Arg Tyr Lys Phe
            20                  25                  30

Arg His Arg Arg Arg Gln Arg Tyr Arg Arg Ala Phe Arg Lys Ala
        35                  40                  45

Phe His Asn Pro Arg Pro Gly Thr Tyr Ser Val Arg Leu Pro Asn Pro
    50                  55                  60

Gln Ser Thr Met Thr Ile Arg Phe Gln Gly Val Ile Phe Leu Thr Glu
65                  70                  75                  80

Gly Leu Ile Leu Pro Lys Asn Ser Thr Ala Gly Tyr Ala Asp His
                85                  90                  95

Met Tyr Gly Ala Arg Val Ala Lys Ile Ser Val Asn Leu Lys Glu Phe
                100                 105                 110

Leu Leu Ala Ser Met Asn Leu Thr Tyr Val Ser Lys Ile Gly Gly Pro
            115                 120                 125

Ile Ala Gly Glu Leu Ile Ala Asp Gly Ser Lys Ser Gln Ala Ala Asp
        130                 135                 140

Asn Trp Pro Asn Cys Trp Leu Pro Leu Asp Asn Asn Val Pro Ser Ala
145                 150                 155                 160

Thr Pro Ser Ala Trp Trp Arg Trp Ala Leu Met Met Met Gln Pro Thr
                165                 170                 175

Asp Ser Cys Arg Phe Phe Asn His Pro Lys Gln Met Thr Leu Gln Asp
            180                 185                 190

Met Gly Arg Met Phe Gly Gly Trp His Leu Phe Arg His Ile Glu Thr
        195                 200                 205

Arg Phe Gln Leu Leu Ala Thr Lys Asn Glu Gly Ser Phe Ser Pro Val
210                 215                 220

Ala Ser Leu Leu Ser Gln Gly Glu Tyr Leu Thr Arg Arg Asp Asp Val
225                 230                 235                 240

Lys Tyr Ser Ser Asp His Gln Asn Arg Trp Gln Lys Gly Gly Gln Pro
                245                 250                 255

Met Thr Gly Gly Ile Ala Tyr Ala Thr Gly Lys Met Arg Pro Asp Glu
            260                 265                 270

Gln Gln Tyr Pro Ala Met Pro Pro Asp Pro Pro Ile Ile Thr Ala Thr
        275                 280                 285

Thr Ala Gln Gly Thr Gln Val Arg Cys Met Asn Ser Thr Gln Ala Trp
290                 295                 300

Trp Ser Trp Asp Thr Tyr Met Ser Phe Ala Thr Leu Thr Ala Leu Gly
305                 310                 315                 320

Ala Gln Trp Ser Phe Pro Pro Gly Gln Arg Ser Val Ser Arg Arg Ser
                325                 330                 335

Phe Asn His His Lys Ala Arg Gly Ala Gly Asp Pro Lys Gly Gln Arg
            340                 345                 350

Trp His Thr Leu Val Pro Leu Gly Thr Glu Thr Ile Thr Asp Ser Tyr
        355                 360                 365
```

```
Met Ser Ala Pro Ala Ser Glu Leu Asp Thr Asn Phe Phe Thr Leu Tyr
    370                 375                 380

Val Ala Gln Gly Thr Asn Lys Ser Gln Gln Tyr Lys Phe Gly Thr Ala
385                 390                 395                 400

Thr Tyr Ala Leu Lys Glu Pro Val Met Lys Ser Asp Ala Trp Ala Val
            405                 410                 415

Val Arg Val Gln Ser Val Trp Gln Leu Gly Asn Arg Gln Arg Pro Tyr
                420                 425                 430

Pro Trp Asp Val Asn Trp Ala Asn Ser Thr Met Tyr Trp Gly Thr Gln
        435                 440                 445

Pro
```

(2) INFORMATION FOR SEQ ID NO:4:

(i) SEQUENCE CHARACTERISTICS:
        (A) LENGTH: 1350 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:4:

```
ATGGCAAGAC GAGCTCGCAG ACCGAGAGGC CGATTTTACT CCTTCAGAAG AGGACGGTGG      60
CACCACCTCA AGCGACTTCG ACGAAGATAT AAATTTCGAC ATCGGAGGAG ACAGCGGTAT     120
CGTAGACGAG CTTTTAGGAA GGCCTTTCAC AACCCCCGCC CCGGTACGTA TAGTGTGAGG     180
CTGCCGAACC CCCAATCTAC TATGACTATC CGCTTCCAAG GGGTCATCTT TCTCACGGAA     240
GGACTCATTC TGCCTAAAAA CAGCACAGCG GGGGGCTATG CAGACCACAT GTACGGGGCG     300
AGAGTCGCCA AGATCTCTGT GAACCTGAAA GAGTTCCTGC TAGCCTCAAT GAACCTGACA     360
TACGTGAGCA AAATCGGAGG CCCCATCGCC GGTGAGTTGA TTGCGGACGG GTCTAAATCA     420
CAAGCCGCGG ACAATTGGCC TAATTGCTGG CTGCCGCTAG ATAATAACGT GCCCTCCGCT     480
ACACCATCGG CATGGTGGAG ATGGGCCTTA ATGATGATGC AGCCCACGGA CTCTTGCCGG     540
TTCTTTAATC ACCCAAAGCA GATGACCCTG CAAGACATGG GTCGCATGTT TGGGGGCTGG     600
CACCTGTTCC GACACATTGA AACCCGCTTT CAGCTCCTTG CCACTAAGAA TGAGGGATCC     660
TTCAGCCCCG TGGCGAGTCT TCTCTCCCAG GGAGAGTACC TCACGCGTCG GGACGATGTT     720
AAGTACAGCA GCGATCACCA GAACCGGTGG CAAAAAGGCG ACAACCGAT GACGGGGGGC      780
ATTGCTTATG CGACCGGGAA AATGAGACCC GACGAGCAAC AGTACCCTGC TATGCCCCCA     840
GACCCCCCGA TCATCACCGC TACTACAGCG CAAGGCACGC AAGTCCGCTG CATGAATAGC     900
ACGCAAGCTT GGTGGTCATG GGACACATAT ATGAGCTTTG CAACACTCAC AGCACTCGGT     960
GCACAATGGT CTTTTCCTCC AGGGCAACGT TCAGTTTCTA GACGGTCCTT CAACCACCAC    1020
AAGGCGAGAG GAGCCGGGGA CCCCAAGGGC CAGAGATGGC ACACGCTGGT GCCGCTCGGC    1080
ACGGAGACCA TCACCGACAG CTACATGTCA GCACCCGCAT CAGAGCTGGA CACTAATTTC    1140
TTTACGCTTT ACGTAGCGCA AGGCACAAAT AAGTCGCAAC AGTACAAGTT CGGCACAGCT    1200
ACATACGCGC TAAAGGAGCC GGTAATGAAG AGCGATGCAT GGGCAGTGGT ACGCGTCCAG    1260
TCGGTCTGGC AGCTGGGTAA CAGGCAGAGG CCATACCCAT GGGACGTCAA CTGGGCGAAC    1320
AGCACCATGT ACTGGGGGAC GCAGCCCTGA                                    1350
```

(2) INFORMATION FOR SEQ ID NO:5:

(i) SEQUENCE CHARACTERISTICS:
        (A) LENGTH: 216 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO:5:

```
Met His Gly Asn Gly Gly Gln Pro Ala Ala Gly Ser Glu Ser Ala
 1               5                  10                  15

Leu Ser Arg Glu Gly Gln Pro Gly Pro Ser Gly Ala Ala Gln Gly Gln
            20                  25                  30

Val Ile Ser Asn Glu Arg Ser Pro Arg Arg Tyr Ser Thr Arg Thr Ile
            35                  40                  45

Asn Gly Val Gln Ala Thr Asn Lys Phe Thr Ala Val Gly Asn Pro Ser
 50                  55                  60

Leu Gln Arg Asp Pro Asp Trp Tyr Arg Trp Asn Tyr Asn His Ser Ile
 65                  70                  75                  80

Ala Val Trp Leu Arg Glu Cys Ser Arg Ser His Ala Lys Ile Cys Asn
                85                  90                  95

Cys Gly Gln Phe Arg Lys His Trp Phe Gln Glu Cys Ala Gly Leu Glu
               100                 105                 110

Asp Arg Ser Thr Gln Ala Ser Leu Glu Glu Ala Ile Leu Arg Pro Leu
               115                 120                 125

Arg Val Gln Gly Lys Arg Ala Lys Arg Lys Leu Asp Tyr His Tyr Ser
           130                 135                 140

Gln Pro Thr Pro Asn Arg Lys Lys Ala Tyr Lys Thr Val Arg Trp Gln
145                 150                 155                 160

Asp Glu Leu Ala Asp Arg Glu Ala Asp Phe Thr Pro Ser Glu Glu Asp
                165                 170                 175

Gly Gly Thr Thr Ser Ser Asp Phe Asp Glu Asp Ile Asn Phe Asp Ile
            180                 185                 190

Gly Gly Asp Ser Gly Ile Val Asp Glu Leu Leu Gly Arg Pro Phe Thr
            195                 200                 205

Thr Pro Ala Pro Val Arg Ile Val
210                 215
```

(2) INFORMATION FOR SEQ ID NO:6:

(i) SEQUENCE CHARACTERISTICS:
        (A) LENGTH: 651 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:6:

```
ATGCACGGGA ACGGCGGACA ACCGGCCGCT GGGGGCAGTG AATCGGCGCT TAGCCGAGAG      60

GGGCAACCTG GCCCAGCGG AGCCGCGCAG GGGCAAGTAA TTTCAAATGA ACGCTCTCCA      120

AGAAGATACT CCACCCGGAC CATCAACGGT GTTCAGGCCA CCAACAAGTT CACGGCCGTT      180

GGAAACCCCT CACTGCAGAG AGATCCGGAT TGGTATCGCT GGAATTACAA TCACTCTATC      240

GCTGTGTGGC TGCGCGAATG CTCGCGCTCC CACGCTAAGA TCTGCAACTG CGGACAATTC      300
```

```
AGAAAGCACT GGTTTCAAGA ATGTGCCGGA CTTGAGGACC GATCAACCCA AGCCTCCCTC        360

GAAGAAGCGA TCCTGCGACC CCTCCGAGTA CAGGGTAAGC GAGCTAAAAG AAAGCTTGAT        420

TACCACTACT CCCAGCCGAC CCCGAACCGC AAAAAGGCGT ATAAGACTGT AAGATGGCAA        480

GACGAGCTCG CAGACCGAGA GGCCGATTTT ACTCCTTCAG AAGAGGACGG TGGCACCACC        540

TCAAGCGACT TCGACGAAGA TATAAATTTC GACATCGGAG GAGACAGCGG TATCGTAGAC        600

GAGCTTTTAG GAAGGCCTTT CACAACCCCC GCCCCGGTAC GTATAGTGTG A                 651
```

(2) INFORMATION FOR SEQ ID NO:7:

(i) SEQUENCE CHARACTERISTICS:
        (A) LENGTH: 121 amino acids
        (B) TYPE: amino acid
        (C) STRANDEDNESS: unknown
        (D) TOPOLOGY: unknown (ii) MOLECULE TYPE: protein (iii) HYPOTHETICAL: NO (xi) SEQUENCE DESCRIPTION: SEQ ID NO:7:

```
Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
            35                  40                  45

Cys Ala Asn Ala Arg Ala Pro Thr Leu Arg Ser Ala Thr Ala Asp Asn
            50                  55                  60

Ser Glu Ser Thr Gly Phe Lys Asn Val Pro Asp Leu Arg Thr Asp Gln
65                  70                  75                  80

Pro Lys Pro Pro Ser Lys Lys Arg Ser Cys Asp Pro Ser Glu Tyr Arg
                85                  90                  95

Val Ser Glu Leu Lys Glu Ser Leu Ile Thr Thr Thr Pro Ser Arg Pro
            100                 105                 110

Arg Thr Ala Lys Arg Arg Ile Arg Leu
            115                 120
```

(2) INFORMATION FOR SEQ ID NO:8:

(i) SEQUENCE CHARACTERISTICS:
        (A) LENGTH: 366 base pairs
        (B) TYPE: nucleic acid
        (C) STRANDEDNESS: unknown
        (D) TOPOLOGY: unknown (ii) MOLECULE TYPE: DNA (genomic)

(iii) HYPOTHETICAL: NO (xi) SEQUENCE DESCRIPTION: SEQ ID NO:8:

```
ATGAACGCTC TCCAAGAAGA TACTCCACCC GGACCATCAA CGGTGTTCAG GCCACCAACA         60

AGTTCACGGC CGTTGGAAAC CCCTCACTGC AGAGAGATCC GGATTGGTAT CGCTGGAATT        120

ACAATCACTC TATCGCTGTG TGGCTGCGCG AATGCTCGCG CTCCCACGCT AAGATCTGCA        180

ACTGCGGACA ATTCAGAAAG CACTGGTTTC AAGAATGTGC CGGACTTGAG GACCGATCAA        240

CCCAAGCCTC CCTCGAAGAA GCGATCCTGC GACCCCTCCG AGTACAGGGT AAGCGAGCTA        300

AAAGAAAGCT TGATTACCAC TACTCCCAGC CGACCCCGAA CCGCAAAAAG GCGTATAAGA        360

CTGTAA                                                                   366
```

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO:9:

```
Glu Asp Thr Pro Pro Gly Pro Ser Thr Val Phe Arg
1               5                   10
```

(2) INFORMATION FOR SEQ ID NO:10:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO:10:

```
Asp Thr Pro Pro Gly Pro Ser Thr Val Phe Arg Pro
1               5                   10
```

(2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO:11:

```
Thr Pro Pro Gly Pro Ser Thr Val Phe Arg Pro Pro
1               5                   10
```

(2) INFORMATION FOR SEQ ID NO:12:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO:12:

```
Pro Pro Gly Pro Ser Thr Val Phe Arg Pro Pro Thr
1               5                   10
```

(2) INFORMATION FOR SEQ ID NO:13:

(i) SEQUENCE CHARACTERISTICS:
        (A) LENGTH: 12 amino acids
        (B) TYPE: amino acid
        (C) STRANDEDNESS: unknown (D) TOPOLOGY: unknown (ii) MOLECULE TYPE: peptide (iii) HYPOTHETICAL: NO (xi) SEQUENCE DESCRIPTION: SEQ ID NO:13:

Pro Gly Pro Ser Thr Val Phe Arg Pro Pro Thr Ser
1               5                   10

(2) INFORMATION FOR SEQ ID NO:14:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:14:

Gly Pro Ser Thr Val Phe Arg Pro Pro Thr Ser Ser
1               5                   10

(2) INFORMATION FOR SEQ ID NO:15:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:15:

Pro Ser Thr Val Phe Arg Pro Pro Thr Ser Ser Arg
1               5                   10

(2) INFORMATION FOR SEQ ID NO:16:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:16:

Gln Glu Cys Ala Gly Leu Glu Asp Arg Ser Thr Gln
1               5                   10

(2) INFORMATION FOR SEQ ID NO:17:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:17:

```
Glu Cys Ala Gly Leu Glu Asp Arg Ser Thr Gln Ala
1               5                   10
```

(2) INFORMATION FOR SEQ ID NO:18:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO:18:

```
Cys Ala Gly Leu Glu Asp Arg Ser Thr Gln Ala Ser
1               5                   10
```

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO:19:

```
Ala Gly Leu Glu Asp Arg Ser Thr Gln Ala Ser Leu
1               5                   10
```

(2) INFORMATION FOR SEQ ID NO:20:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO:20:

```
Gly Leu Glu Asp Arg Ser Thr Gln Ala Ser Leu Glu
1               5                   10
```

(2) INFORMATION FOR SEQ ID NO:21:

(i) SEQUENCE CHARACTERISTICS:
        (A) LENGTH: 12 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO:21:

```
Pro Ser Thr Val Phe Arg Pro Pro Thr Ser Ser Arg
1               5                   10
```

(2) INFORMATION FOR SEQ ID NO:22:

(i) SEQUENCE CHARACTERISTICS:
        (A) LENGTH: 12 amino acids

```
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:22:

Ser Thr Val Phe Arg Pro Pro Thr Ser Ser Arg Pro
1               5                   10

(2) INFORMATION FOR SEQ ID NO:23:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:23:

Thr Val Phe Arg Pro Pro Thr Ser Ser Arg Pro Leu
1               5                   10

(2) INFORMATION FOR SEQ ID NO:24:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:24:

Val Phe Arg Pro Pro Thr Ser Ser Arg Pro Leu Glu
1               5                   10

(2) INFORMATION FOR SEQ ID NO:25:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:25:

Phe Arg Pro Pro Thr Ser Ser Arg Pro Leu Glu Thr
1               5                   10

(2) INFORMATION FOR SEQ ID NO:26:

(i) SEQUENCE CHARACTERISTICS:
            (A) LENGTH: 12 amino acids
            (B) TYPE: amino acid
            (C) STRANDEDNESS:
            (D) TOPOLOGY: unknown (ii) MOLECULE TYPE: peptide (iii) HYPOTHETICAL: NO
```

(xi) SEQUENCE DESCRIPTION: SEQ ID NO:26:

Arg Pro Pro Thr Ser Ser Arg Pro Leu Glu Thr Pro
1               5                   10

(2) INFORMATION FOR SEQ ID NO:27:

(i) SEQUENCE CHARACTERISTICS:
            (A) LENGTH: 12 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:27:

Pro Pro Thr Ser Ser Arg Pro Leu Glu Thr Pro His
1               5                   10

(2) INFORMATION FOR SEQ ID NO:28:

(i) SEQUENCE CHARACTERISTICS:
            (A) LENGTH: 6 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:28:

Pro Ser Thr Val Phe Arg
1               5

(2) INFORMATION FOR SEQ ID NO:29:

(i) SEQUENCE CHARACTERISTICS:
            (A) LENGTH: 8 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:29:

Gly Leu Glu Asp Arg Ser Thr Gln
1               5

(2) INFORMATION FOR SEQ ID NO:30:

(i) SEQUENCE CHARACTERISTICS:
            (A) LENGTH: 5 amino acids
            (B) TYPE: amino acid
            (C) STRANDEDNESS: unknown
            (D) TOPOLOGY: unknown (ii) MOLECULE TYPE: peptide (iii) HYPOTHETICAL: NO (xi) SEQUENCE DESCRIPTION: SEQ ID NO:30:

Pro Thr Ser Ser Arg
1               5